US006262118B1

(12) United States Patent
Luskey et al.

(10) Patent No.: US 6,262,118 B1
(45) Date of Patent: Jul. 17, 2001

(54) USE OF (-) (3-TRIHALOMETHYLPHENOXY) (4-HALOPHENYL) ACETIC ACID DERIVATIVES FOR TREATMENT OF INSULIN RESISTANCE, TYPE 2 DIABETES AND HYPERLIPIDEMIA

(75) Inventors: Kenneth L. Luskey, Saratoga; Jian Luo, Brisbane, both of CA (US)

(73) Assignee: MetaBolex, Inc., Hayward, CA (US)

( * ) Notice: Subject to any disclaimer, the term of this patent is extended or adjusted under 35 U.S.C. 154(b) by 0 days.

(21) Appl. No.: 09/325,997

(22) Filed: Jun. 4, 1999

(51) Int. Cl.$^7$ .................................................. A61K 31/20

(52) U.S. Cl. ............................................................ 514/559

(58) Field of Search ............................................... 514/559

(56) References Cited

U.S. PATENT DOCUMENTS

| | | | |
|---|---|---|---|
| 3,517,050 | 6/1970 | Bolhofer | 260/473 |
| 3,923,855 | 12/1975 | Shuman | 260/456 R |
| 3,953,490 | 4/1976 | Shuman | 260/465 F |
| 4,067,996 | 1/1978 | Najer et al. | 424/308 |
| 4,146,623 | 3/1979 | Parker | 424/248.52 |
| 5,859,051 | 1/1999 | Adams et al. | 514/469 |
| 5,883,124 | 3/1999 | Samid | 514/538 |

FOREIGN PATENT DOCUMENTS

| | | |
|---|---|---|
| 967978 | 5/1975 | (CA) . |
| 1 182 008 | 2/1970 | (GB) . |
| WO 92 17435 | 10/1992 | (WO) . |

OTHER PUBLICATIONS

Aronow, W. et al., "Effect of halofenate on serum lipids," *Clin. Pharmacol. Ther.*, 14(1):358–365 (1973).
Bardin, C.W., eds., Current Therapy in Endocrinology and Metabolism, 6$^{th}$ Edition, Mosby–Year Book, Inc., St. Louis, MO (1997).
Barrett–Conner, E., "Epidemiology, Obesity, and Non–Insulin–Dependant Diabetes Mellitus," *Epidemol. Rev.*, 11:172–181 (1989).
Bell, G. et al., "Glucokinase Mutations, Insulin Secretion, and Diabetes Mellitus," *Annu. Rev. Physiol.*, 58:171–186 (1996).
Chiasson, J. et al., "The Efficacy of Acarbose in the Treatment of Patients with Non–Insulin–dependant Diabetes Mellitus," *Ann. Intern. Med.*, 121:928–935 (1994).
Coniff, R. et al., "Acarbose: A Review of US Clinical Experience," *Clin. Ther.*, 19(1):16–26 (1997).
Coniff, R. et al., "Multicenter, Placebo–Controlled Trial Comparing Acarbose (BAY g 5421) With Placebo, Tolbutamide, and Tolbutamide–Plus–Acarbose in Non–Insulin–Dependant Diabetes Mellitus," *Am. J. Med.*, 98:443–451 (1995).
Edelman et al., "Non–Insulin–Dependant Diabetes Mellitus," Curr. Therapy Endocrin. Metabol., sixth edition, pp. 430–438, published by Mosby–Year Book, Inc. (1997).

Fajans S. et al., "Maturity Onset Diabetes of the Young," *Diabet. Med.*, 13:S90–S95 (1996).
Flier, J. "Insulin Receptors and Insulin Resistance," *Ann Rev. Med.*, 34:145–160 (1983).
Friedberg, S.J., "The Control of Insulin Resistant and Refractory Type II Diabetes Mellitus by Means of Halofenate–Sulfonylurea Combined Regimen," *Clin. Res.*, 34(2): 682A (1986).
Goetze et al., "PPAR gamma–ligands inhibit migration mediated by multiple chemoattractants in vascular smooth muscle cells," *J. Cardiovasc. Pharmacol.*, 33(5):798–806 (1999).
Howard B. et al., "Lipoprotein Composition in Diabetes Mellitus," *Artherosclerosis*, 30:153–162 (1978).
Hucker et al., "Metabolism of a New Hypolipidemic Agent, 2–Acetamidoethyl (p–Chlorophenyl) (m–Trifluoromethylphenoxy)–Acetate (Halofenate) In The Rat, Dog, Rhesus Monkey and Man," *J. Pharm. Exp. Ther.*, 179(2):359–371 (1971).
Iwamoto, Y. et al., "Effect of Combination Therapy of Troglitazone and Sulphonylureas in Patients with type 2 Diabetes Who Were Poorly Controlled by Sulphonylurea Therapy Alone," *Diabet. Med.*, 13:365–370 (1996).
Jain, A. et al., "Potentiation of Hypoglycemic Effect of Sulfonylureas by Halofenate," *N. Eng. J. Med.*, 293(25):1283–1286 (1975).
Joslin, E., "Arteriosclerosis and Diabetes," *Ann. Chin. Med.*, 5(12):1061–1079 (1927).
Knowler, et al., "Obesity in the Pima Indians: its magnitude and relationship with diabetes," *Am. J. Clin. Nutr.*, 53:1543S–1551S (1991).
Kohl, E. et al., "Improved control of Non–insulin–dependant Diabetes Mellitus by Combined Halofenate and Chloropropamide Therapy," *Diabetes Care*, 7(1):19–24 (1984).
Kreisberg, R.A., "Hyperlipidemia," Curr. Therapy Endocrin. Metabol., sixth edition, pp. 509–519, published by Mosby–Year Book, Inc. (1997).
Kudzma et al., "Potentiation of Hypoglycemic Effect of Chlorpropamide and Phenformin by Halofenate," *Diabetes*, 25(4):291–95 (1977).
Kwiterovich, P. "State–of–the–Art Update and Review: Clinical Trials of Lipid–Lowering Agents," *Am. J. Cardiol.*, 82(12A):3U–17U (1998).
LeRoith, D. et al., (eds.), Diabetes Mellitus, Lippincott–Raven Publishers, Philadelphia, PA U.S.A. (1996).
Lin, J.H. et al., "Inhibition and Induction of Cytochrome P450 and the Clinical Implications," *Clin. Pharmacokinet*, 35(5):361–390 (1998).

(List continued on next page.)

Primary Examiner—Rebecca Cook
(74) Attorney, Agent, or Firm—Townsend and Townsend and Crew LLP

(57) ABSTRACT

The present invention provides the use of (−) (3-trihalomethylphenoxy) (4-halophenyl) acetic acid derivatives and compositions in the treatment of insulin resistance, Type 2 diabetes and hyperlipidemia.

11 Claims, 15 Drawing Sheets-

OTHER PUBLICATIONS

Mahler, R. et al., "Clinical Review 102 Type 2 Diabetes Mellitus: Update on Diagnosis, Pathophysiology, and Treatment," *J. Clin. Endocrinol. Metab.*, 84(4):1165–1171 (1999).

McMahon, F.G. et al., "Some Effects of MK–185 on Lipid and Uric Acid Metabolism in Man," *Univ. Mich. Med. Center J.*, 36(4):247–248 (1970).

Miners, J. O. et al., "Cytochrome P4502C9: an enzyme of major importance in human drug metabolism," *Bri. J. Clin. Pharmacol.*, 45:525–538 (1998).

Morgan, J.P. et al., "Hypolipidemic, uricosuric, and thyroxine–displacing effects of MK–185 (halofenate)," *Clin. Pharmacol. Therap.*, 12(3):517–524 (1971).

Pelkonen, O. et al., "Inhibition and induction of human cytochrome P450 (CYP) enzymes," *Xenobiotica*, 28(12):1203–1253 (1998).

Reaven, G. M. "Insulin Resistance and Human Disease: A Short History," *J. Basic & Clin. Phys. & Pharm.*, 9:387–406 (1998).

Reaven, G. M. "Pathophysiology of Insulin Resistance in Human Disease," *Physiol. Rev.*, 75(3):473–486 (1995).

Sirtori, C. et al., "Clinical Evaluation of MK–185: A New Hypolipidemic Drug1," *Lipids*, 7(2):96–99 (1972).

Skyler, J.S., "Glucose Control in Type 2 Diabetes Mellitus," *Ann. Int. Med.*, 127(9):837–838 (1997).

Steiner et al., "A Comparative Review of the Adverse Effects of Treatments for Hyperlipidaemia," *Drug Safety*, 6(2):118–130 (1991).

Taskinen et al., "Lipid disorders in NIDDM: implications for treatment," *J. Int. Med.*, 244:361–370 (1998).

Trust et al., "(Aryloxy)[p–(arloxy)phenyl]– and (arloxy)[–(arylthio)phenyl] acetic acids and esters as hypolipidemic agents," *J. Med. Chem.*, 22(9):1068–1074 (1979).

Turner et al., "Insulin resistance, impaired glucose tolerance and non–insulin–dependant diabetes, pathologic mechanisms and treatment: Current status and therapeutic possibilities," *Process in Drug Res.*, 51:34–94 (1998).

Vesell, E. S. et al., "Differential Effects of Chronic Halofenate Administration on Drug Metabolism in Man," *Fed. Proc.*, 31(2):538 (1972).

Wilson, J. et al., (ed.), "Disorders of Lipid Metabolism," Chapter 23, *Textbook of Endocrinology*, 9th Edition, W.B. Sanders Company, Philadelphia, PA U.S.A (1998).

Wright et al., "UKPDS 28: A Randomized Trial of Efficacy of Early Addition of Metformin in Sulfonylurea–Treated Type 2 Diabetes," *Diabetes Care*, 21(1):87–92; (1998).

The Expert Committee on the Diagnosis and Classification of Diabetes Mellitus, "Report of the Expert Committee on the Diagnosis and Classification of Diabetes Mellitus," *Diabetes Care*, 22 (Suppl 1): S5–19 (1999).

Feldman E.B., et al. "Insulin sensitivity in hypertriglyceridemia: induction by combined triglyceride and uric acid lowereing," Clinical Research vol. 23, No. 1, p.43A (1975).

Feldman E.B., et al. "Effects of halofenate on glucose tolerance in patients with hyperlipoproteinemia," Journal of Clinical Pharmacology vol.18, May–Jun., pp. 241–248 (1978).

Berkow and Fletcher, "*The Merk manual of diagnosis and therapy–15th edition*," pp. 1069–1072, Merk Sharp & Dohme Research Laboratories, N.J. (1987).

Schapel G.J., et al., Efficacy and Interactions of Oxandroione and Clofibrate in Factorial Study on Experimental Acute Nephrotic Hyper Lipidemia, *Journal of Pharmacology and Experimental Therapeutics*, 194(1) 274–284 (1975).

Ryan, R.J., "The Metabolic Spectrum of Halofenate", *Journal of Clinical Pharmacology and Biopharmacy*, 12(1–2) 239–243 (Jul. 1995).

Aronow, W.S., et al. "Halofenate Effective Hypouricemia–Inducing Drug", *Current Therapeutic Research–Clinical and Experimental*, 15(12) 902–906 (1973).

Hutchison, J.C. et al., "The Uricosuric Action of the Halofenate (MK 185) in Patients with Hyperuricemia or Uncomplicated Primary Gout and Hyperlipidemia", *Atherosclerosis*, 18:353–362 (1973).

USE OF (−) (3-TRIHALOMETHYLPHENOXY) (4-HALOPHENYL) ACETIC ACID DERIVATIVES FOR TREATMENT OF INSULIN RESISTANCE, TYPE 2 DIABETES AND HYPERLIPIDEMIA

FIELD OF THE INVENTION

The present invention relates to the use of (−) (3-trihalomethylphenoxy) 4-halophenyl) acetic acid derivatives and compositions in the treatment of insulin resistance, Type 2 diabetes and hyperlipidemia.

BACKGROUND OF THE INVENTION

Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996), and all references cited therein. According to the American Diabetes Association, diabetes mellitus is estimated to affect approximately 6% of the world population. Uncontrolled hyperglycemia is associated with increased and premature mortality due to an increased risk for microvascular and macrovascular diseases, including nephropathy, neuropathy, retinopathy, hypertension, cerebrovascular disease and coronary heart disease. Therefore, control of glucose homeostasis is a critically important approach for the treatment of diabetes.

There are two major forms of diabetes: Type 1 diabetes (formerly referred to as insulin-dependent diabetes or IDDM); and Type 2 diabetes (formerly referred to as non-insulin dependent diabetes or NIDDM).

Type 1 diabetes is the result of an absolute deficiency of insulin, the hormone which regulates glucose utilization. This insulin deficiency is usually characterized by β-cell destruction within the Islets of Langerhans in the pancreas, which usually leads to absolute insulin deficiency. Type 1 diabetes has two forms: Immune-Mediated Diabetes Mellitus, which results from a cellular mediated autoimmune destruction of the β cells of the pancreas; and Idiopathic Diabetes Mellitus, which refers to forms of the disease that have no known etiologies.

Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequately control glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese patients and lipid oxidation is increased.

Premature development of atherosclerosis and increased rate of cardiovascular and peripheral vascular diseases are characteristic features of patients with diabetes. Hyperlipidemia is an important precipitating factor for these diseases. Hyperlipidemia is a condition generally characterized by an abnormal increase in serum lipids in the bloodstream and is an important risk factor in developing atherosclerosis and heart disease. For a review of disorders of lipid metabolism, see, e.g., Wilson, J. et al., (ed.), Disorders of Lipid Metabolism, Chapter 23, Textbook of Endocrinology, $9^{th}$ Edition, (W. B. Sanders Company, Philadelphia, Pa. U.S.A. 1998; this reference and all references cited therein are herein incorated by reference). Serum lipoproteins are the carriers for lipids in the circulation. They are classified according to their density: chylomicrons; very low-density lipoproteins (VLDL); intermediate density lipoproteins (IDL); low density lipoproteins (LDL); and high density lipoproteins (HDL). Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia. Elevated cholesterol levels are associated with a number of disease states, including coronary artery disease, angina pectoris, carotid artery disease, strokes, cerebral arteriosclerosis, and xanthoma.

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, E. *Ann. Chim. Med.* (1927) 5: 1061–1079). Epidemiological studies since then have confirmed the association and have shown a several-fold increase in coronary deaths among diabetic subjects when compared with nondiabetic subjects (see, e.g., Garcia, M. J. et al., *Diabetes* (1974) 23: 105–11 (1974); and Laakso, M. and Lehto, S., *Diabetes Reviews* (1997) 5(4): 294–315). Several lipoprotein abnormalities have been described among diabetic subjects (Howard B., et al., *Artherosclerosis* (1978) 30: 153–162).

Previous studies from the 1970's have demonstrated the effectiveness of racemic 2-acetamidoethyl (4-chlorophenyl) (3-trifluoromethylphenoxy) acetate (also known as "halofenate") as a potential therapeutic agent to treat Type 2 diabetes and hyperlipidemia (see, e.g., Bolhofer, W., U.S. Pat. No. 3,517,050; Jain, A. et al., *N. Eng. J Med.* (1975) 293: 1283–1286; Kudzma, D. et al, *Diabetes* (1977) 25: 291–95; Kohl, E. et al., *Diabetes Care* (1984) 7: 19–24; McMahon, F. G. et al., *Univ. Mich. Med. Center J.* (1970) 36: 247–248; Simori, C. et al., *Lipids* (1972) 7: 96–99; Morgan, J. P. et al., *Clin. Pharmacol. Therap.* (1971) 12: 517–524 and Aronow, W. S. et al, *Clin. Pharmacol Ther* (1973) 14: 358–365). In these previous studies, the effect of racemic halofenate on diabetes was observed when combined with sulfonylureas. A minimal effect on glucose was observed in patients with diabetes treated with racemic halofenate alone. However, significant side effects were noted including gastrointestinal bleeding from stomach and peptic ulcers (see, e.g., Friedberg, S. J. et al., *Clin. Res.* (1986) Vol. 34, No. 2: 682A).

In addition, there were some indications of drug-drug interactions of racemic halofenate with agents such as warfarin sulfate (also referred to as 3-(alpha-acetonylbenzyl)-4-hydroxycoumarin or Coumadin™ (Dupont Pharmaceuticals, E.I. Dupont de Nemours and Co., Inc., Wilmington, Del. U.S.A.) (see, e.g., Vesell, E. S. and Passantanti, G. T., *Fed. Proc.* (1972) 31(2): 538). Coumadin™ is an anticoagulant that acts by inhibiting the synthesis of vitamin K dependent clotting factors (which include Factors II, VII, IX, and X, and the anticoagulant proteins C and S). Coumadin™ is believed to be stereospecifically metabolized by hepatic microsomal enzymes (the cytochrome P450 enzymes). The cytochrome P450 isozymes involved in the metabolism of Coumadin include 2C9, 2C19, 2C8, 2C18, 1A2, and 3A4. 2C9 is likely to be the principal form of human liver P450 which modulates in vivo drug metabolism of several drugs including the anticoagulant activity of Coumadin™ (see, e.g., Miners, J. O. et al, *Bri. J. Clin. Pharmacol.* (1998) 45: 525–538).

Drugs that inhibit the metabolism of Coumadin™ result in a further decrease in vitamin K dependent clotting factors that prevents coagulation more than desired in patients receiving such therapy (i.e., patients at risk for pulmonary or cerebral embolism from blood clots in their lower extremities, heart or other sites). Simple reduction of the dose of anticoagulant is often difficult as one needs to maintain adequate anticoagulation to prevent blood clots from forming. The increased anticoagulation from drug-drug interaction results in a significant risk to such patients with the possibility of severe bleeding from soft tissue injuries, gastrointestinal sites (i.e., gastric or duodenal ulcers) or other lesions (i.e., aortic aneurysm). Bleeding in the face of too much anticoagulation constitutes a medical emergency and can result in death if it is not treated immediately with appropriate therapy.

Cytochrome P450 2C9 is also known to be involved in the metabolism of several other commonly used drugs, including dilantin, sulfonylureas, such as tolbutamide and several nonsteroidal anti-inflammatory agents, such as ibuprofen. Inhibition of this enzyme has the potential to cause other adverse effects related to drug-drug interactions, in addition to those described above for Coumadin™ (see, e.g., Pelkonen, O. et al., *Xenobiotica* (1998) 28: 1203–1253; Linn, J. H. and Lu, A. Y., *Clin. Pharmacokinet.* (1998) 35(5): 361–390).

Solutions to the above difficulties and deficiencies are needed before halofenate becomes effective for routine treatment of insulin resistance, Type 2 diabetes and hyperlipidemia. The present invention fulfills this and other needs by providing compositions and methods for alleviating insulin resistance, Type 2 diabetes and hyperlipidemia, while presenting a better adverse effect profile.

SUMMARY OF THE INVENTION

This present invention provides a method of modulating Type 2 diabetes in a mammal. The method comprises administering to the mammal a therapeutically effective amount of the (−) stereoisomer of a compound of Formula I,

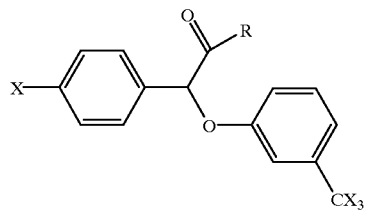

wherein R is a member selected from the group consisting of a hydroxy, lower aralkoxy, di-lower alkylamino-lower alkoxy, lower alkanamido lower alkoxy, benzamido-lower alkoxy, ureido-lower alkoxy, N'-lower alkyl-ureido-lower alkoxy, carbamoyl-lower alkoxy, halophenoxy substituted lower alkoxy, carbamoyl substituted phenoxy, carbonyl-lower alkylamino, N,N-di-lower alkylamino-lower alkylamino, halo substituted lower alkylamino, hydroxy substituted lower alkylamino, lower alkanolyloxy substituted lower alkylamino, ureido, and lower alkoxycarbonylamino; and X is a halogen; or a pharmaceutically acceptable salt thereof, wherein the compound is substantially free of its (+) stereoisomer.

Some such methods further comprise a compound of Formula II:

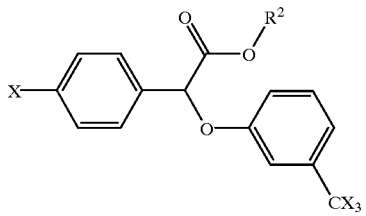

wherein $R^2$ is a member selected from the group consisting of phenyl-lower alkyl, lower alkanamido-lower alkyl, and benzamido-lower alkyl.

Some such methods further comprise a compound of Formula III:

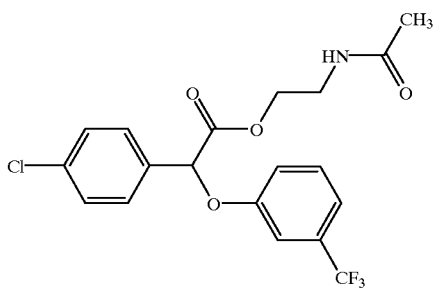

The preferred compound of Formula III is known as "(−)2-acetamidoethyl 4-chlorophenyl-(3-trifluoromethylphenoxy)-acetate" or "(−)halofenate."

The present invention further provides a method for modulating insulin resistance in a mammal. This method comprises administering to the mammal a therapeutically effective amount of the (−) stereoisomer of a compound of Formula I. Some such methods further comprise a compound of Formula II. Some such methods further comprise a compound of Formula III.

The present invention further provides a method of alleviating hyperlipidemia in a mammal. This method comprises administering to the mammal a therapeutically effective amount of a compound of Formula I. Some such methods further comprise a compound of Formula II. Some such methods further comprise a compound of Formula III.

The present invention also provides pharmaceutical compositions. The pharmaceutical compositions comprise a pharmaceutically acceptable carrier and a therapeutically effective amount of a compound of Formula I, Formula II or Formula III.

BRIEF DESCRIPTION OF THE DRAWINGS

relative to a vehicle treated control group. In the animals treated with the high dose, the (−) enantiomer resulted in the greatest extent of cholesterol lowering.

DEFINITIONS

Figure 1:
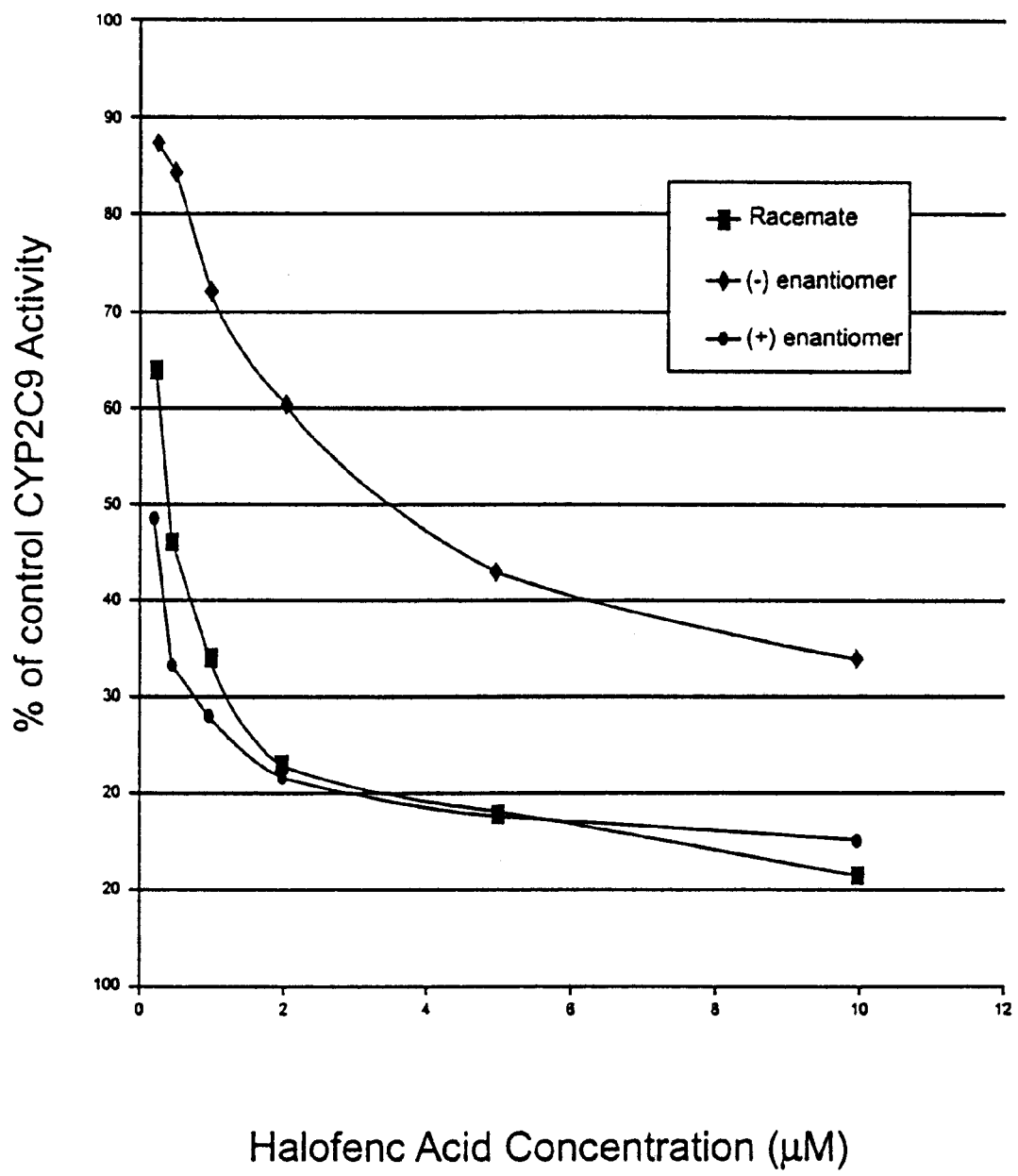
FIG. 1 shows the inhibition of cytochrome P450 2C9 (CYP2C9) activity by racemic halofenic acid, (−) halofenic acid and (+) halofenic acid. The hydroxylation of tolbutamide was measured in the presence of increasing concentrations of these compounds. Racemic halofenic acid inhibited CYP 2C9 activity with an IC50 of 0.45 $\mu$M and (+) halofenic acid inhibited CYP 2C9 with an IC50 of 0.22 $\mu$M. In contrast, the (−) halofenic acid was 20-fold less potent with an apparent IC50 of 3.5 $\mu$M.

The term "mammal" includes, without limitation, humans, domestic animals (e.g., dogs or cats), farm animals (cows, horses, or pigs), monkeys, rabbits, mice, and laboratory animals.

The term "insulin resistance" can be defined generally as a disorder of glucose metabolism. More specifically, insulin resistance can be defined as the diminished ability of insulin to exert its biological action across a broad range of concentrations producing less than the expected biologic effect. (see, e.g., Reaven, G. M., *J. Basic & Clin. Phys. & Pharm.* (1998) 9: 387–406 and Flier, J. *Ann Rev. Med.* (1983) 34:145–60). Insulin resistant persons have a diminished ability to properly metabolize glucose and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, Impaired Glucose Tolerance (IGT), gestational diabetes, hypertension, obesity, atherosclerosis and a variety of other disorders. Eventually, the insulin resistant individuals can progress to a point where a diabetic state is reached. The association of insulin resistance with glucose intolerance, an increase in plasma triglyceride and a decrease in high-density lipoprotein cholesterol concentrations, high blood pressure, hyperuricemia, smaller denser low-density lipoprotein particles, and higher circulating levels of plaminogen activator inhibitor-1), has been referred to as "Syndrome X" (see, e.g., Reaven, G. M., *Physiol. Rev.* (1995) 75: 473–486).

The term "diabetes mellitus" or "diabetes" means a disease or condition that is generally characterized by metabolic defects in production and utilization of glucose which result in the failure to maintain appropriate blood sugar levels in the body. The result of these defects is elevated blood glucose, referred to as "hyperglycemia." Two major forms of diabetes are Type 1 diabetes and Type 2 diabetes. As described above, Type 1 diabetes is generally the result of an absolute deficiency of insulin, the hormone which regulates glucose utilization. Type 2 diabetes often occurs in the face of normal, or even elevated levels of insulin and can result from the inability of tissues to respond appropriately to insulin. Most Type 2 diabetic patients are insulin resistant and have a relative deficiency of insulin, in that insulin secretion can not compensate for the resistance of peripheral tissues to respond to insulin. In addition, many Type 2 diabetics are obese. Other types of disorders of glucose homeostasis include Impaired Glucose Tolerance, which is a metabolic stage intermediate between normal glucose homeostasis and diabetes, and Gestational Diabetes Mellitus, which is glucose intolerance in pregnancy in women with no previous history of Type 1 or Type 2 diabetes.

The term "secondary diabetes" is diabetes resulting from other identifiable etiologies which include: genetic defects of β cell function (e.g., maturity onset-type diabetes of youth, referred to as "MODY," which is an early-onset form of Type 2 diabetes with autosomal inheritance; see, e.g., Fajans S. et al., *Diabet. Med.* (1996) (9 Suppl 6): S90-5 and Bell, G. et al., *Annu. Rev. Physiol.* (1996) 58: 171–86; genetic defects in insulin action; diseases of the exocrine pancreas (e.g., hemochromatosis, pancreatitis, and cystic fibrosis); certain endocrine diseases in which excess hormones interfere with insulin action (e.g., growth hormone in acromegaly and cortisol in Cushing's syndrome); certain drugs that suppress insulin secretion (e.g., phenytoin) or inhibit insulin action (e.g., estrogens and glucocorticoids); and diabetes caused by infection (e.g., rubella, Coxsackie, and CMV); as well as other genetic syndromes.

The guidelines for diagnosis for Type 2 diabetes, impaired glucose tolerance, and gestational diabetes have been outlined by the American Diabetes Association (see, e.g., The Expert Committee on the Diagnosis and Classification of Diabetes Mellitus, *Diabetes Care,* (1999) Vol 2 (Suppl 1): S5-19).

The term "halofenic acid" refers to the acid form of 4-Chlorophenyl-(3-trifluoromethylphenoxy)-acetic acid.

The term "hyperinsulinemia" refers to the presence of an abnormally elevated level of insulin in the blood.

The term "secretagogue" means a substance or compound that stimulates secretion. For example, an insulin secretagogue is a substance or compound that stimulates secretion of insulin.

The term "hemoglobin" or "Hb" refers to a respiratory pigment present in erythrocytes, which is largely responsible for oxygen transport. A hemoglobin molecule comprises four polypeptide subunits (two α chain systems and two β chain systems, respectively). Each subunit is formed by association of one globin protein and one heme molecule which is an iron-protoporphyrin complex. The major class of hemoglobin found in normal adult hemolysate is adult hemoglobin (referred to as "HbA"; also referred to HbA$_0$ for distinguishing it from glycated hemoglobin, which is referred to as "HbA$_1$," described infra) having $\alpha_2\beta_2$ subunits. Trace components such as HbA$_2$ ($\alpha_2\delta_2$) can also be found in normal adult hemolysate.

Among classes of adult hemoglobin HbAs, there is a glycated hemoglobin (referred to as "HbA$_1$," or "glycosylated hemoglobin"), which may be further fractionated into HbA$_{1a1}$, RbA$_{1a2}$, HbA$_{1b}$, and HbA$_{1c}$ with an ion exchange resin fractionation. All of these subclasses have the same primary structure, which is stabilized by formation of an aldimine (Schiff base) by the amino group of N-terminal valine in the β subunit chain of normal hemoglobin HbA and glucose (or, glucose-6-phosphate or fructose) followed by formation of ketoamine by Amadori rearrangement.

The term "glycosylated hemoglobin" (also referred to as "HbA$_{1c}$,", "GHb", "hemoglobin- glycosylated", "diabetic control index" and "glycohemoglobin"; hereinafter referred to as "hemoglobin A$_{1c}$") refers to a stable product of the nonenzymatic glycosylation of the β-chain of hemoglobin by plasma glucose. Hemoglobin $A_{1c}$ comprises the main portion of glycated hemoglobins in the blood. The ratio of glycosylated hemoglobin is proportional to blood glucose level. Therefore, hemoglobin $A_{1c}$ rate of formation directly increases with increasing plasma glucose levels. Since glycosylation occurs at a constant rate during the 120-day lifespan of an erythrocyte, measurement of glycosylated hemoglobin levels reflect the average blood glucose level for an individual during the preceding two to three months. Therefore determination of the amount of glycosylated hemoglobin $HbA_{1c}$ can be a good index for carbohydrate metabolism control. Accordingly, blood glucose levels of the last two months can be estimated on the basis of the ratio of $HbA_{1c}$ to total hemoglobin Hb. The analysis of the hemoglobin $A_{1c}$ in blood is used as a measurement enabling long-term control of blood glucose level (see, e.g., Jain, S., et al., *Diabetes* (1989) 38: 1539–1543; Peters A., et al., *JAMA* (1996) 276: 1246–1252).

The term "symptom" of diabetes, includes, but is not limited to, polyuria, polydipsia, and polyphagia, as used herein, incorporating their common usage. For example, "polyuria" means the passage of a large volume of urine during a given period; "polydipsia" means chronic, excessive thirst; and "polyphagia" means excessive eating. Other symptoms of diabetes include, e.g., increased susceptibility to certain infections (especially fungal and staphylococcal infections), nausea, and ketoacidosis (enhanced production of ketone bodies in the blood).

The term "complication" of diabetes includes, but is not limited to, microvascular complications and macrovascular complications. Microvascular complications are those complications which generally result in small blood vessel damage. These complications include, e.g., retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys). Macrovascular complications are those complications which generally result from large blood vessel damage. These complications include, e.g., cardiovascular disease and peripheral vascular disease. Cardiovascular disease refers to diseases of blood vessels of the heart. See. e.g., Kaplan, R. M., et al., "Cardiovascular diseases" in HEALTH AND HUMAN BEHAVIOR, pp. 206–242 (McGraw-Hill, New York 1993). Cardiovascular disease is generally one of several forms, including, e.g., hypertension (also referred to as high blood pressure), coronary heart disease, stroke, and rheumatic heart disease. Peripheral vascular disease refers to diseases of any of the blood vessels outside of the heart. It is often a narrowing of the blood vessels that carry blood to leg and arm muscles.

The term "atherosclerosis" encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease".

The term "antihyperlipidemic" refers to the lowering of excessive lipid concentrations in blood to desired levels.

The term "hyperlipidemia" refers to the presence of an abnormally elevated level of lipids in the blood. Hyperlipidemia can appear in at least three forms: (1) hypercholesterolemia, i.e., an elevated cholesterol level; (2) hypertriglyceridemia, i.e., an elevated triglyceride level; and (3) combined hyperlipidemia, i.e., a combination of hypercholesterolemia and hypertriglyceridemia.

The term "modulate" refers to the treating, prevention, suppression, enhancement or induction of a function or condition. For example, the compounds of the present invention can modulate hyperlipidemia by lowering cholesterol in a human, thereby suppressing hyperlipidemia.

The term "treating" means the management and care of a human subject for the purpose of combating the disease, condition, or disorder and includes the administration of a compound of the present invention to prevent the onset of the symptoms or complications, alleviating the symptoms or complications, or eliminating the disease, condition, or disorder.

The term "cholesterol" refers to a steroid alcohol that is an essential component of cell membranes and myelin sheaths and, as used herein, incorporates its common usage. Cholesterol also serves as a precursor for steroid hormones and bile acids.

The term "triglyceride(s)" ("TGs"), as used herein, incorporates its common usage. TGs consist of three fatty acid molecules esterified to a glycerol molecule and serve to store fatty acids which are used by muscle cells for energy production or are taken up and stored in adipose tissue.

Because cholesterol and TGs are water insoluble, they must be packaged in special molecular complexes known as "lipoproteins" in order to be transported in the plasma. Lipoproteins can accumulate in the plasma due to overproduction and/or deficient removal. There are at least five distinct lipoproteins differing in size, composition, density, and function. In the cells of the small of the intestine, dietary lipids are packaged into large lipoprotein complexes called "chylomicrons", which have a high TG and low-cholesterol content. In the liver, TG and cholesterol esters are packaged and released into plasma as TG-rich lipoprotein called very low density lipoprotein ("VLDL"), whose primary function is the endogenous transport of TGs made in the liver or released by adipose tissue. Through enzymatic action, VLDL can be either reduced and taken up by the liver, or transformed into intermediate density lipoprotein ("IDL"). IDL, is in turn, either taken up by the liver, or is further modified to form the low density lipoprotein ("LDL"). LDL is either taken up and broken down by the liver, or is taken up by extrahepatic tissue. High density lipoprotein ("HDL") helps remove cholesterol from peripheral tissues in a process called reverse cholesterol transport.

The term "dyslipidemia" refers to abnormal levels of lipoproteins in blood plasma including both depressed and/or elevated levels of lipoproteins (e.g., elevated levels of LDL, VLDL and depressed levels of HDL).

Exemplary Primary Hyperlipidemia include, but are not limited to, the following:
  (1) Familial Hyperchylomicronemia, a rare genetic disorder which causes a deficiency in an enzyme, LP lipase, that breaks down fat molecules. The LP lipase deficiency can cause the accumulation of large quantities of fat or lipoproteins in the blood;
  (2) Familial Hypercholesterolemia, a relatively common genetic disorder caused where the underlying defect is a series of mutations in the LDL receptor gene that result in malfunctioning LDL receptors and/or absence of the LDL receptors. This brings about ineffective clearance of LDL by the LDL receptors resulting in elevated LDL and total cholesterol levels in the plasma;

(3) Familial Combined Hyperlipidemia, also known as multiple lipoprotein-type hyperlipidemia; an inherited disorder where patients and their affected first-degree relatives can at various times manifest high cholesterol and high triglycerides. Levels of HDL cholesterol are often moderately decreased;

(4) Familial Defective Apolipoprotein B-100 is a relatively common autosomal dominant genetic abnormality. The defect is caused by a single nucleotide mutation that produces a substitution of glutamine for arginine which can cause reduced affinity of LDL particles for the LDL receptor. Consequently, this can cause high plasma LDL and total cholesterol levels;

(5) Familial Dysbetaliproteinemia, also referred to as Type III Hyperlipoproteinemia, is an uncommon inherited disorder resulting in moderate to severe elevations of serum TG and cholesterol levels with abnormal apolipoprotein E function. HDL levels are usually normal; and (6) Familial Hypertriglyceridemia, is a common inherited disorder in which the concentration of plasma VLDL is elevated. This can cause mild to moderately elevated triglyceride levels (and usually not cholesterol levels) and can often be associated with low plasma HDL levels.

Risk factors in exemplary Secondary Hyperlipidemia include, but are not limited to, the following: (1) disease risk factors, such as a history of Type 1 diabetes, Type 2 diabetes, Cushing's syndrome, hypothroidism and certain types of renal failure; (2) drug risk factors, which include, birth control pills; hormones, such as estrogen, and corticosteroids; certain diuretics; and various β blockers; (3) dietary risk factors include dietary fat intake per total calories greater than 40%; saturated fat intake per total calories greater than 10%; cholesterol intake greater than 300 mg per day; habitual and excessive alcohol use; and obesity.

The terms "obese" and "obesity" refers to, according to the World Health Organization, a Body Mass Index (BMI) greater than 27.8 kg/m$^2$ for men and 27.3 kg/m$^2$ for women (BMI equals weight (kg)/height (m$^2$). Obesity is linked to a variety of medical conditions including diabetes and hyperlipidemia. Obesity is also a known risk factor for the development of Type 2 diabetes (See, e.g., Barrett-Conner, E., *Epidemol. Rev.* (1989) 11: 172–181; and Knowler, et al., *Am. J Clin. Nutr.* (1991) 53:1543–1551).

"Pharmaceutically acceptable salts" refer to the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the compounds of the present invention with a suitable organic or inorganic acid. Representative salts include, but are not limited to, the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate, and the like.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. For a description of pharmaceutically acceptable acid addition salts as prodrugs. See, e.g., Bundgaard, H., ed., *Design of Prodrugs* (Elsevier Science Publishers, Amsterdam 1985).

"Pharmaceutically acceptable ester" refers to those esters which retain, upon hydrolysis of the ester bond, the biological effectiveness and properties of the carboxylic acid or alcohol and are not biologically or otherwise undesirable. For a description of pharmaceutically acceptable esters as prodrugs, see Bundgaard, H., supra. These esters are typically formed from the corresponding carboxylic acid and an alcohol. Generally, ester formation can be accomplished via conventional synthetic techniques. (See, e.g., March *Advanced Organic Chemistry,* 3rd Ed., p. 1157 (John Wiley & Sons, New York 1985) and references cited therein, and Mark et al., *Encyclopedia of Chemical Technology,* (1980) John Wiley & Sons, New York). The alcohol component of the ester will generally comprise: (i) a $C_2$–$C_{12}$ aliphatic alcohol that can or can not contain one or more double bonds and can or can not contain branched carbons; or (ii) a $C_7$–$C_{12}$ aromatic or heteroaromatic alcohols. The present invention also contemplates the use of those compositions which are both esters as described herein and at the same time are the pharmaceutically acceptable acid addition salts thereof.

"Pharmaceutically acceptable amide" refers to those amides which retain, upon hydrolysis of the amide bond, the biological effectiveness and properties of the carboxylic acid or amine and are not biologically or otherwise undesirable. For a description of pharmaceutically acceptable amides as prodrugs, see, Bundgaard, H., ed., supra. These amides are typically formed from the corresponding carboxylic acid and an amine. Generally, amide formation can be accomplished via conventional synthetic techniques. See, e.g., March et al., *Advanced Organic Chemistry,* 3rd Ed., p. 1152 (John Wiley & Sons, New York 1985), and Mark et al., *Encyclopedia of Chemical Technology,* (John Wiley & Sons, New York 1980). The present invention also contemplates the use of those compositions which are both amides as described herein and at the same time are the pharmaceutically acceptable acid addition salts thereof.

DETAILED DESCRIPTION

(1) General

The present invention is directed to use of a preferred (−) (3-trihalomethylphenoxy) (4-halophenyl) acetic acid derivatives having the following general formula:

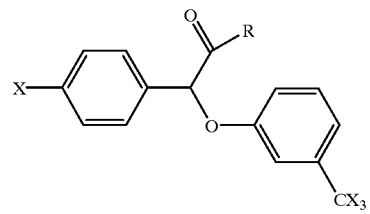

Formula I

In Formula I, R is a functional group including, but not limited to, the following: hydroxy, lower aralkoxy, e.g., phenyl-lower alkoxy such as benzyloxy, phenethyloxy; di-lower alkylamino-lower alkoxy and the nontoxic, pharmacologically acceptable acid addition salts thereof, e.g., dimethylaminoethoxy, diethylaminoethoxy hydrochloride, diethylaminoethoxy citrate, diethylaminopropoxy; lower alkanamido lower alkoxy, e.g., formamidoethoxy, acetamidoethoxy or acetamidopropoxy; benzamido-lower alkoxy, e.g., benzamidoethoxy or benzamidopropoxy; ureido-lower alkoxy, e.g., ureidoethoxy or 1-methyl-2-ureidoethoxy; N'-lower alkyl-ureido-lower alkoxy, i.e., $R^1NH—CONH—C_nH_{2n}—O—$ wherein $R^1$ represents lower alkyl and n is an integer having a value of from 1 to about 5, e.g., N'-ethyl-ureidoethoxy or N'-ethyl-ureidopropoxy; carbamoyl-lower alkoxy, e.g., carbamoylmethoxy or carbamoylethoxy; halophenoxy substituted lower alkoxy, e.g., 2-(4-chlorophenoxy) ethoxy or 2- (4-chlorophenoxy)-2-methylpropoxy; carbamoyl substituted phenoxy, e.g., 2-carbamoylphenoxy; carboxy-lower alkylamino and the nontoxic, pharmacologically acceptable amine addition salts thereof, e.g., carboxymethylamino cyclohexylamine salt or carboxyethylamine; N,N-di-lower alkylamino-lower alkylamino and the nontoxic, pharmacologically acceptable acid solution salts thereof, e.g., N,N-dimethylaminoethylamino hydrochloride, N,N-diethylaminoethylamino, N,N-diethylaminoethylamino citrate, or N,N-dimethylaminopropylamino citrate; halo substituted lower alkylamino, e.g., 2-chloroethylamino or 4-chlorobutylamino; hydroxy substituted lower alkylamino, e.g., 2-hydroxyethylamino, or 3-hydroxypropylamino; lower alkanoyloxy substituted lower alkylamino, e.g., acetoxyethylamino or acetoxypropylamino; ureido; lower alkoxycarbonylamino, e.g., methoxycarbonylamino (i.e., $—NHCOOCH_3$), or ethyoxycarbonylamino (i.e., $CHCOOC_2H_5$). In a preferred embodiment, R is selected such that it is a hydrolyzable moiety, such as an ester or amide, and upon hydrolysis of the ester or amide bond, the compound is biologically active such as pharmaceutically acceptable esters or amides as prodrugs. X, in formula I, is a halogen, e.g., chloro, bromo, fluoro or iodo.

In a preferred embodiment, the present invention relates to use of the (−)(3-trihalomethylphenoxy)(4-halophenyl) acetic acid derivatives having the following general formula:

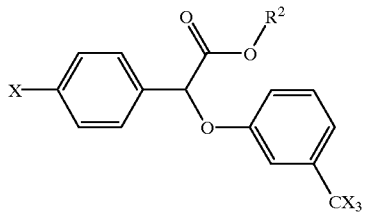

Formula II

In Formula II, $R^2$ is a functional group including, but not limited to, the following: hydrogen, phenyl-lower alkyl, e.g., benzyl; lower alkanamido-lower alkyl, e.g., acetamidoethyl; or benzamido-lower alkyl, e.g., benzamidoethyl. X, in Formula II, is a halogen, e.g., chloro, bromo, fluoro or iodo.

In a further preferred embodiment, the present invention relates to the use of a compound having the formula:

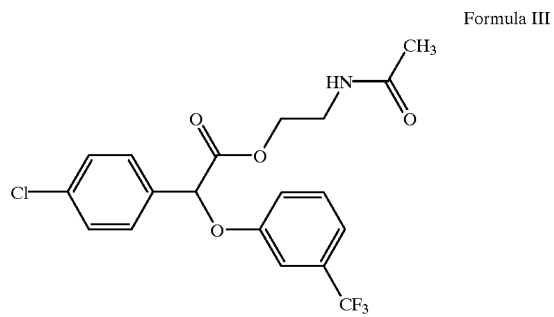

Formula III

The compound of Formula III is referred to as "(−)2-acetamidoethyl 4-chlorophenyl-(3-trifluoromethylphenoxy) acetate" (also referred to as "(−) halofenate").

Changes in drug metabolism mediated by inhibition of cytochrome P450 enzymes has a very high potential to precipitate significant adverse effects in patients. Such effects were previously noted in patients treated with racemic halofenate. In the present studies, racemic halofenic acid was found to inhibit cytochrome P450 2C9, an enzyme known to play a significant role in the metabolism of specific drugs. This can lead to significant problems with drug interactions with anticoagulants, anti-inflammatory agents and other drugs metabolized by this enzyme. However, quite surprisingly, a substantial difference was observed between the enantiomers of halofenic acid in their inability to inhibit cytochrome P450 2C9, the (−) enantiomer being about twenty-fold less active whereas the (+) enantiomer was quite potent (see Example 7). Thus, use of the (−) enantiomer of compounds in Formula I, Formula II or Formula III will avoid the inhibition of this enzyme and the adverse effects on drug metabolism previously observed with racemic halofenate.

The present invention encompasses a method of modulating insulin resistance in a mammal, the method comprising: administering to the mammal a therapeutically effective amount of a compound having the general structure of Formula I or a pharmaceutically acceptable salt thereof. In a presently preferred embodiment, the compound has the general structure of Formula II. In a further preferred embodiment, the compound has the structure of Formula III. Quite surprisingly, the method avoids the adverse effects associated with the administration of a racemic mixture of halofenate by providing an amount of the (−) stereoisomer of the compounds in Formula I, Formula II or Formula III which is insufficient to cause the adverse effects associated with the inhibition of cytochrome P450 2C9.

The present invention also encompasses a method of modulating Type 2 diabetes in a mammal, the method comprising: administering to the mammal a therapeutically effective amount of a compound having the general structure of Formula I or a pharmaceutically acceptable salt thereof In a presently preferred embodiment, the compound has the general structure of Formula II. In a further preferred embodiment, the compound has the structure of Formula III. Quite surprisingly, the method avoids the adverse effects associated with the administration of a racemic mixture of halofenate by providing an amount of the (−) stereoisomer of the compounds in Formula I, Formula II or Formula III which is insufficient to cause the adverse effects associated with the inhibition of cytochrome P450 2C9.

The present invention further encompasses a method of modulating hyperlipidemia in a mammal, the method comprising: administering to the mammal a therapeutically effective amount of a compound having the general structure of Formula I or a pharmaceutically acceptable salt thereof. In a presently preferred embodiment, the compound has the general structure of Formula II. In a further preferred embodiment, the compound has the structure of Formula III. Quite surprisingly, the method avoids the adverse effects associated with the administration of a racemic mixture of halofenate by providing an amount of the (−) stereoisomer of the compounds in Formula I, Formula II or Formula III which is insufficient to cause the adverse effects associated with the inhibition of cytochrome P450 2C9.

The racemic mixture of the halofenate (i.e., a 1:1 racemic mixture of the two enantiomers) possesses antihyperlipidemic activity and provides therapy and a reduction of hyperglycemia related to diabetes when combined with certain other drugs commonly used to treat this disease. However, this racemic mixture, while offering the expectation of efficacy, causes adverse effects. The term "adverse effects" includes, but is not limited to, nausea, gastrointestinal ulcers, and gastrointestinal bleeding. Other side effects that have been reported with racemic halofenate include potential problems with drug-drug interactions, especially including difficulties controlling anticoagulation with Coumadin™. Utilizing the substantially pure compounds of the present invention results in clearer dose related definitions of efficacy, diminished adverse effects, and accordingly, an improved therapeutic index. As such, it has now been discovered that it is more desirable and advantageous to administer the (−) enantiomer of halofenate instead of racemic halofenate.

(2)(−) Enantiomers of Formula I, Formula II and Formula III

Many organic compounds exist in optically active forms, i.e., they have the ability to rotate the plane of plane-polarized light. In describing an optically active compound, the prefixes R and S are used to denote the absolute configuration of the molecule about its chiral center(s). The prefixes "d" and "l" or (+) and (−) are employed to designate the sign of rotation of plane-polarized light by the compound, with (−) or l meaning that the compound is "levorotatory" and with (+) or d is meaning that the compound is "dextrorotatory". There is no correlation between nomenclature for the absolute stereochemistry and for the rotation of an enantiomer. For a given chemical structure, these compounds, called "stereoisomers," are identical except that they are mirror images of one another. A specific stereoisomer can also be referred to as an "enantiomer," and a mixture of such isomers is often called an "enantiomeric" or "racemic" mixture. See, e.g., Streitwiesser, A. & Heathcock, C. H., INTRODUCTION TO ORGANIC CHEMISTRY, $2^{nd}$ Edition, Chapter 7 (MacMillan Publishing Co., U.S.A. 1981).

The chemical synthesis of the racemic mixture of halofenates (3-trihalomethylphenoxy)(4-halophenyl) acetic acid derivatives can be performed by the methods described in U.S. Pat. No. 3,517,050, the teaching of which are incorporated herein by reference. The synthesis of the compounds of the present invention is further described in the Examples, supra. The individual enantiomers can be obtained by resolution of the racemic mixture of enantiomers using conventional means known to and used by those of skill in the art. See, e.g., Jaques, J., et al., in ENANTIOMERS, RACEMATES, AND RESOLUTIONS, John Wiley and Sons, New York (1981). Other standard methods of resolution known to those skilled in the art, including but not limited to, simple crystallization and chromatographic resolution, can also be used (see, e.g., STEREOCHEMISTRY OF CARBON COMPOUNDS (1962) E. L. Eliel, McGraw Hill; Lochmuller, J. *Chromatography* (1975) 113, 283–302). Additionally, the compounds of the present invention, i.e., the optically pure isomers, can be prepared from the racemic mixture by enzymatic biocatalytic resolution. Enzymatic biocatalytic resolution has been described previously (see, e.g., U.S. Pat. Nos. 5,057,427 and 5,077,217, the disclosures of which are incorporated herein by reference). Other methods of obtaining enantiomers include stereospecific synthesis (see, e.g., Li, A. J. et al., *Pharm. Sci.* (1997) 86:1073–1077).

The term "substantially free of its (+) stereoisomer," as used herein, means that the compositions contain a substantially greater proportion of the (−) isomer of halofenate in relation to the (+) isomer. In a preferred embodiment, the term "substantially free of its (+) stereoisomer," as used herein, means that the composition is at least 90% by weight of the (−) isomer and 10% by weight or less of the (+) isomer. In a more preferred embodiment, the term "substantially free of its (+) stereoisomer," as used herein, means that the composition contains at least 99% by weight of the (−) isomer and 1% by weight or less of the (+) isomer. In the most preferred embodiment, the term "substantially free of its (+) stereoisomer," means that the composition contains greater than 99% by weight of the (−) isomer. These percentages are based upon the total amount of halofenate in the composition. The terms "substantially optically pure (l) isomer of halofenate," "substantially optically pure (l) halofenate," "optically pure (l) isomer of halofenate" and "optically pure (l) halofenate" all refer to the (−) isomer and are encompassed by the above-described amounts. In addition, the terms "substantially optically pure (d) isomer of halofenate," "substantially optically pure (d) halofenate," "optically pure (d) isomer of halofenate" and "optically pure (d) halofenate" all refer to the (+) isomer and are encompassed by the above-described amounts.

The term "enantiomeric excess" or "ee" is related to the term "optical purity" in that both are measures of the same phenomenon. The value of ee will be a number from 0 to 100, 0 being racemic and 100 being pure, single enantiomer. A compound that is referred to as 98% optically pure can be described as 96% ee.

(3) Combination Therapy With Additional Active Agents

The compositions can be formulated and administered in the same manner as detailed below. "Formulation" is defined as a pharmaceutical preparation that contains a mixture of various excipients and key ingredients that provide a relatively stable, desirable and useful form of a compound or drug. For the present invention, "formulation" is included within the meaning of the term "composition." The compounds of the present invention can be used effectively alone or in combination with one or more additional active agents depending on the desired target therapy (see, e.g., Turner, N. et al. *Prog. Drug Res.* (1998) 51: 33–94; Haffner, S. *Diabetes Care* (1998) 21: 160–178; and DeFronzo, R. et al. (eds.), *Diabetes Reviews* (1997) Vol. 5 No. 4). A number of studies have investigated the benefits of combination therapies with oral agents (see, e.g., Mahler, R., *J. Clin. Endocrinol. Metab.* (1999) 84: 1165–71; United Kingdom Prospective Diabetes Study Group: UKPDS 28, Diabetes Care (1998) 21: 87–92; Bardin, C. W.,(ed.), CURRENT THERAPY IN ENDOCRINOLOGY AND METABOLISM, $6^{th}$ Edition (Mosby—Year Book, Inc., St. Louis, Mo. 1997);

Chiasson, J. et al., *Ann. Intern. Med.* (1994) 121: 928–935; Coniff, R. et al., *Clin. Ther.* (1997) 19: 16–26; Coniff, R. et al., *Am. J. Med.* (1995) 98: 443–451; and Iwamoto, Y. et al, *Diabet. Med.* (1996) 13 365–370; Kwiterovich, P. *Am. J. Cardiol* (1998) 82(12A): 3U–17U). These studies indicate that diabetes and hyperlipidemia modulation can be further improved by the addition of a second agent to the therapeutic regimen. Combination therapy includes administration of a single pharmaceutical dosage formulation which contains a compound having the general structure of Formula I (or Formula II or Formula III) and one or more additional active agents, as well as administration of a compound of Formula I (or Formula II or Formula III) and each active agent in its own separate pharmaceutical dosage formulation. For example, a compound of Formula I and an HMG-CoA reductase inhibitor can be administered to the human subject together in a single oral dosage composition, such as a tablet or capsule, or each agent can be administered in separate oral dosage formulations. Where separate dosage formulations are used, a compound of Formula I and one or more additional active agents can be administered at essentially the same time (i.e., concurrently), or at separately staggered times (i.e., sequentially). Combination therapy is understood to include all these regimens.

An example of combination therapy that modulates (prevents the onset of the symptoms or complications associated) atherosclerosis, wherein a compound of Formula I is administered in combination with one or more of the following active agents: an antihyperlipidemic agent; a plasma HDL-raising agent; an antihypercholesterolemic agent, such as a cholesterol biosynthesis inhibitor, e.g., an hydroxymethylglutaryl (HMG) CoA reductase inhibitor (also referred to as statins, such as lovastatin, simvastatin, pravastatin, fluvastatin, and atorvastatin), an HMG-CoA synthase inhibitor, a squalene epoxidase inhibitor, or a squalene synthetase inhibitor (also known as squalene synthase inhibitor); an acyl-coenzyme A cholesterol acyltransferase (ACAT) inhibitor, such as melinamide; probucol; nicotinic acid and the salts thereof and niacinamide; a cholesterol absorption inhibitor, such as β-sitosterol; a bile acid sequestrant anion exchange resin, such as cholestyramine, colestipol or dialkylaminoalkyl derivatives of a cross-linked dextran; an LDL (low density lipoprotein) receptor inducer; fibrates, such as clofibrate, bezafibrate, fenofibrate, and gemfibrozil; vitamin $B_6$ (also known as pyridoxine) and the pharmaceutically acceptable salts thereof, such as the HCl salt; vitamin $B_{12}$ (also known as cyanocobalamin); vitamin $B_3$ (also known as nicotinic acid and niacinamide, supra); anti-oxidant vitamins, such as vitamin C and E and beta carotene; a beta-blocker; an angiotensin II antagonist; an angiotensin converting enzyme inhibitor; and a platelet aggregation inhibitor, such as fibrinogen receptor antagonists (i.e., glycoprotein IIb/IIIa fibrinogen receptor antagonists) and aspirin. As noted above, the compounds of Formula I can be administered in combination with more than one additional active agent, for example, a combination of a compound of Formula I with an HMG-CoA reductase inhibitor (e.g., lovastatin, simvastatin and pravastatin) and aspirin, or a compound of Formula I with an HMG-CoA reductase inhibitor and a β blocker.

Another example of combination therapy can be seen in treating obesity or obesity-related disorders, wherein the compounds of Formula I can be effectively used in combination with, for example, phenylpropanolamine, phentermine, diethylpropion, mazindol; fenfluramine, dexfenfluramine, phentiramine, $\beta_3$ adrenoceptor agonist agents; sibutramine, gastrointestinal lipase inhibitors (such as orlistat), and leptins. Other agents used in treating obesity or obesity-related disorders wherein the compounds of Formula I can be effectively used in combination with, for example, neuropeptide Y, enterostatin, cholecytokinin, bombesin, amylin, histamine $H_3$ receptors, dopamine $D_2$ receptors, melanocyte stimulating hormone, corticotrophin releasing factor, galanin and gamma amino butyric acid (GABA).

Still another example of combination therapy can be seen in modulating diabetes (or treating diabetes and its related symptoms, complications, and disorders), wherein the compounds of Formula I can be effectively used in combination with, for example, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone); dehydroepiandrosterone (also referred to as DHEA or its conjugated sulphate ester, DHEA-$SO_4$); antiglucocorticoids; TNFα inhibitors; α-glucosidase inhibitors (such as acarbose, miglitol, and voglibose), pramlintide (a synthetic analog of the human hormone amylin), other insulin secretogogues (such as repaglinide, gliquidone, and nateglinide), insulin, as well as the active agents discussed above for treating atherosclerosis.

A further example of combination therapy can be seen in modulating hyperlipidemia (treating hyperlipidemia and its related complications), wherein the compounds of Formula I can be effectively used in combination with, for example, statins (such as fluvastatin, lovastatin, pravastatin or simvastatin), bile acid-binding resins (such as colestipol or cholestyramine), nicotinic acid, probucol, betacarotene, vitamin E, or vitamin C.

In accordance with the present invention, a therapeutically effective amount of a compound of Formula I (or Formula II or Formula III) can be used for the preparation of a pharmaceutical composition useful for treating diabetes, treating hyperlipidemia, treating obesity, lowering triglyceride levels, lowering cholesterol levels, raising the plasma level of high density lipoprotein, and for treating, preventing or reducing the risk of developing atherosclerosis.

Additionally, an effective amount of a compound of Formula I (or Formula II or Formula III) and a therapeutically effective amount of one or more active agents selected from the group consisting of: an antihyperlipidemic agent; a plasma HDL-raising agent; an antihypercholesterolemic agent, such as a cholesterol biosynthesis inhibitor, for example, an HMG-CoA reductase inhibitor, an HMG-CoA synthase inhibitor, a squalene epoxidase inhibitor, or a squalene synthetase inhibitor (also known as squalene synthase inhibitor); an acyl-coenzyme A cholesterol acyltransferase inhibitor; probucol; nicotinic acid and the salts thereof; niacinamide; a cholesterol absorption inhibitor; a bile acid sequestrant anion exchange resin; a low density lipoprotein receptor inducer; clofibrate, fenofibrate, and gemfibrozil; vitamin $B_6$ and the pharmaceutically acceptable salts thereof; vitamin $B_{12}$; an anti-oxidant vitamin; a β-blocker; an angiotensin II antagonist; an angiotensin converting enzyme inhibitor; a platelet aggregation inhibitor; a fibrinogen receptor antagonist; aspirin; phentiramines, $\beta_3$ adrenergic receptor agonists; sulfonylureas, biguanides, α-glucosidase inhibitors, other insulin secretogogues, and insulin can be used together for the preparation of a pharmaceutical composition useful for the above-described treatments.

(4) Pharmaceutical Formulations and Methods of Administration

In the methods of the present present invention, the compounds of Formula I, Formula II, and Formula III can be delivered or administered to a mammal, e.g., a human patient or subject, alone, in the form of a pharmaceutically acceptable salt or hydrolyzable precursor thereof, or in the form of a pharmaceutical composition where the compound is mixed with suitable carriers or excipient(s) in a therapeutically effective amount. By a "therapeutically effective dose", "therapeutically effective amount", or, interchangeably, "pharmacologically acceptable dose" or "pharmacologically acceptable amount", it is meant that a sufficient amount of the compound of the present invention, alternatively, a combination, for example, a compound of the present invention, which is substantially free of its (+) stereoisomer, and a pharmaceutically acceptable carrier, will be present in order to achieve a desired result, e.g., alleviating a symptom or complication of Type 2 diabetes.

The compounds of Formula I, Formula II, and Formula III that are used in the methods of the present invention can be incorporated into a variety of formulations for therapeutic administration. More particularly, the compounds of Formula I (or Formula II or Formula III) can be formulated into pharmaceutical compositions by combination with appropriate, pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intratracheal administration. Moreover, the compound can be administered in a local rather than systemic manner, in a depot or sustained release formulation. In addition, the compounds can be administered in a liposome.

In addition, the compounds of Formula I, Formula II or Formula III can be formulated with common excipients, diluents or carriers, and compressed into tablets, or formulated as elixirs or solutions for convenient oral administration, or administered by the intramuscular or intravenous routes. The compounds can be administered transdermally, and can be formulated as sustained release dosage forms and the like.

Compounds of Formula I, Formula II, or Formula III can be administered alone, in combination with each other, or they can be used in combination with other known compounds (discussed supra). In pharmaceutical dosage forms, the compounds can be administered in the form of their pharmaceutically acceptable salts thereof. They can contain hydrolyzable moieties. They can also be used alone or in appropriate association, as well as in combination with, other pharmaceutically active compounds.

Suitable formulations for use in the present invention are found in *Remington's Pharmaceutical Sciences* (Mack Publishing Company (1985) Philadelphia, Pa., 17th ed.), which is incorporated herein by reference. Moreover, for a brief review of methods for drug delivery, see, Langer, *Science* (1990) 249:1527–1533, which is incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds of the present invention can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds of Formula I, Formula II, or Formula III can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions or emulsions in oily or aqueous vehicles, and can contain formulator agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter, carbowaxes, polyethylene glycols or other glycerides, all of which melt at body temperature, yet are solidified at room temperature.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds can be employed. Liposomes and emulsions are well known examples of delivery vehicles or carriers for hydrophobic drugs. In a presently preferred embodiment, long-circulating, i.e., stealth, liposomes can be employed. Such liposomes are generally described in Woodle, et al., U.S. Pat. No. 5,013,556, the teaching of which is hereby incorporated by reference. The compounds of the present invention can also be administered by controlled release means and/or delivery devices such as those described in U.S. Pat. Nos. 3,845,770; 3,916,899; 3,536,809; 3,598,123; and 4,008,719; the disclosures of which are hereby incorporated by reference.

Certain organic solvents such as dimethylsulfoxide (DMSO) also can be employed, although usually at the cost of greater toxicity. Additionally, the compounds can be delivered using a sustained-release system, such as semipermeable matrices of solid hydrophobic polymers containing the therapeutic agent. Various types of sustained-release materials have been established and are well known by those skilled in the art. Sustained-release capsules can, depending on their chemical nature, release the compounds for a few hours up to over 100 days.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in the method of the present invention, a therapeutically effective dose can be estimated initially from cell culture assays or animal models.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds which exhibit high therapeutic indices are preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition. (See, e.g., Fingl et al. 1975 In: *The Pharmacological Basis of Therapeutics,* Ch. 1).

The amount of active compound that can be combined with a carrier material to produce a single dosage form will vary depending upon the disease treated, the mammalian species, and the particular mode of administration. However, as a general guide, suitable unit doses for the compounds of the present invention can, for example, preferably contain between 100 mg to about 3000 mg of the active compound. A preferred unit dose is between 500 mg to about 1500 mg. A more preferred unit dose is between 500 to about 1000 mg. Such unit doses can be administered more than once a day, for example 2, 3, 4, 5 or 6 times a day, but preferably 1 or 2 times per day, so that the total daily dosage for a 70 kg adult is in the range of 0.1 to about 250 mg per kg weight of subject per administration. A preferred dosage is 5 to about 250 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those of skill in the area.

A typical dosage can be one 10 to about 1500 mg tablet taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to interrupt, adjust, or terminate therapy in conjunction with individual patient response.

(5) Protecting Groups

Certain compounds having the general structure of Formula I and II may require the use of protecting groups to enable their successful elaboration into the desired structure. Protecting groups can be chosen with reference to Greene, T. W., et al., *Protective Groups in Organic Synthesis,* John Wiley & Sons, Inc., 1991. The blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenation.

Examples of suitable hydroxyl protecting groups are: trimethylsilyl, triethylsilyl, o-nitrobenzyloxycarbonyl, p-nitrobenzyloxycarbonyl, t-butyldiphenylsilyl, t-butyldimethylsilyl, benzyloxycarbonyl, t-butyloxycarbonyl, 2,2,2-trichloroethyloxycarbonyl, and allyloxycarbonyl. Examples of suitable carboxyl protecting groups are benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl.

(6) Process

The process for making the compounds of the present invention is generally depicted in Scheme 1 (and further described in the Examples):

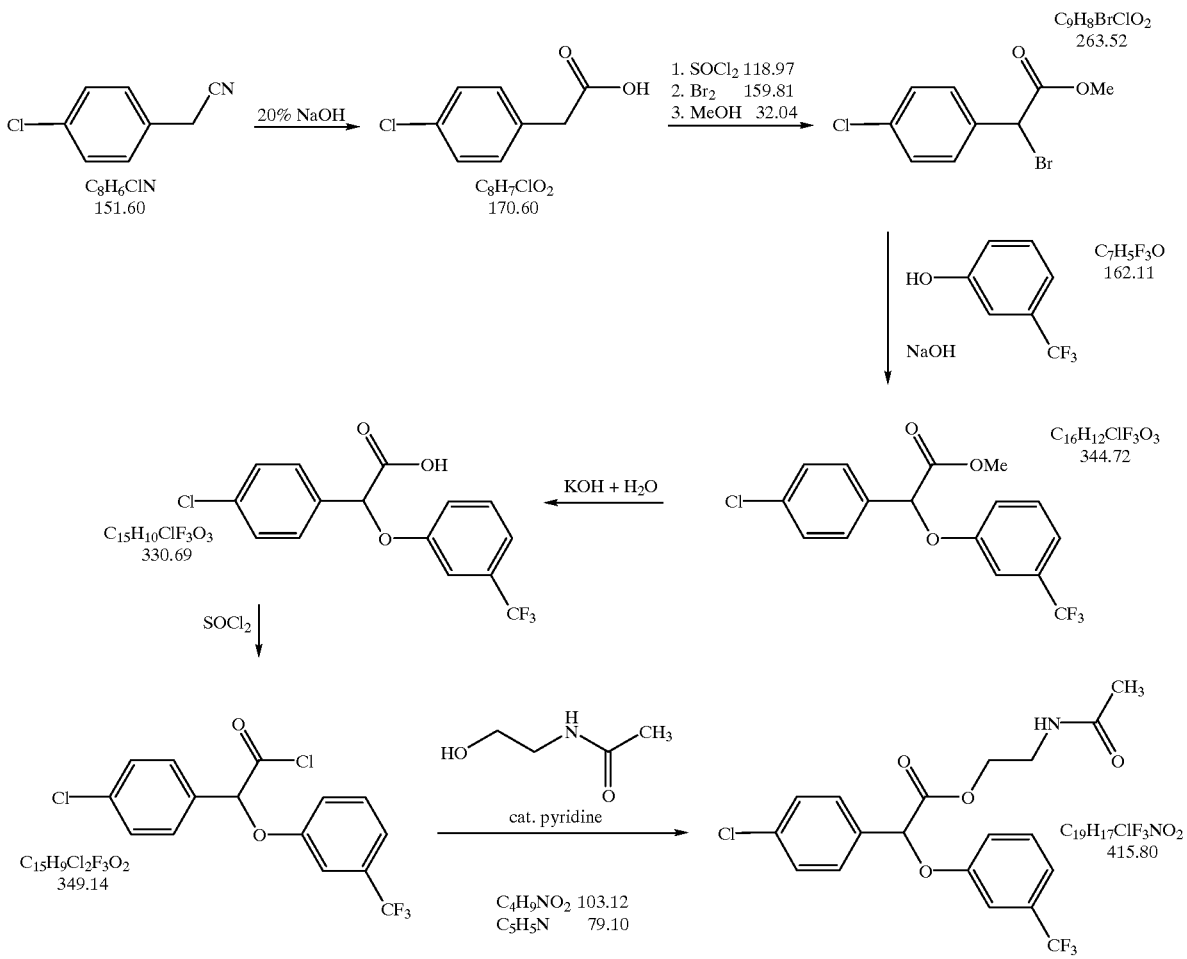

Scheme 1

The stereoisomers of the compounds of the present invention can be prepared by using reactants or reagents or catalysts in their single enantiomeric form in the process wherever possible or by resolving the mixture of stereoisomers by conventional methods, discussed supra and in the Examples. Some of the preferred methods include use of microbial resolution, resolving the diastereomeric salts formed with chiral acids or chiral bases.

(7) Kits

In addition, the present invention provides for kits with unit doses of the compounds of Formula I, Formula II, or Formula III either in oral or injectable doses. In addition to the containers containing the unit doses will be an informational package insert describing the use and attendant benefits of the drugs in alleviating symptoms and/or complications associated with Type 2 diabetes as well as in alleviating hyperlipidemia. Preferred compounds and unit doses are those described herein above.

EXAMPLES

The compounds of Formula I, Formula II, or Formula III of the present invention can be readily prepared using the process set forth in Scheme 1, supra, and from the following examples.

Example 1

This example relates to the preparation of Methyl Bromo-(4-chlorophenyl)acetate.

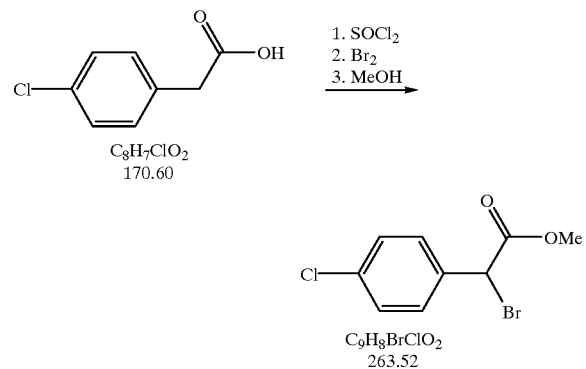

The initial compound listed in Scheme 1, i.e., 4-chlorophenylacetic acid, is readily available from several commercial sources (e.g., Aldrich and Fluka).

A 5-L Morton reactor equipped with a magnetic stirrer, a pot temperature control, and addition funnel was vented through a gas scrubber and charged with p-chlorophenylacetic acid (720 gm, 4.2 moles) and $SOCl_2$ (390 ml, 630 gm, 5.3 moles). The reaction was stirred, heated and held at 55°±5° C. for 1 hour. Bromine (220 ml., 670 gm, 5.3 moles) was then added over 20 min. and stirred at 55°±5° C. for 16 hours. The temperature was raised to 80° C. for 7 hours and then cooled to 9° C. in an ice-water bath. Methanol (2.0 L, 1.6 kg, 49.4 moles) was then carefully added. The solvent was stripped to obtain 2 liquids weighing 1.28 kg. These were dissolved in a mixture of 0.84 L water and 2.1 L ether and separated. The organic phase was washed once with 0.78 L 25% (w:w) aqueous NaCl and dried over 0.13 kg $MgSO_4$. This was filtered through Whatman #1 filter paper and stripped of solvent to obtain 0.985 kg of orange liquid. The proton NMR showed this to be 80% product and 19% non-brominated ester. The HPLC showed 82% product and 18% non-brominated ester. HPLC was run on a Zorbax SB-C8 column at 30° C. measuring 250×4.6 mm and 5µ particle size. The mobile phase was 60:40 (v:v) acetonitrile: 0.1% $H_3PO_4$ at 1.5 ml/min. Detection was at 210 nm. The injected sample of 1 µl was dissolved in acetonitrile at a concentration of 10 mg/ml. The product had a retention time of 5.0 min. and that of the non-brominated ester was 3.8 min. This crude product was purified by vacuum distillation to obtain 96% pure product with an 84% yield. The product proton NMR ($CDCl_3$, 300 MHz) showed shifts at 3.79 (s, 3H), 5.32 (s, 1H) and 7.20–7.55 (m, 4H) ppm.

Example 2

This example relates to the preparation of Methyl 4-Chlorophenyl-(3-trifluoromethylphenoxy)-acetate.

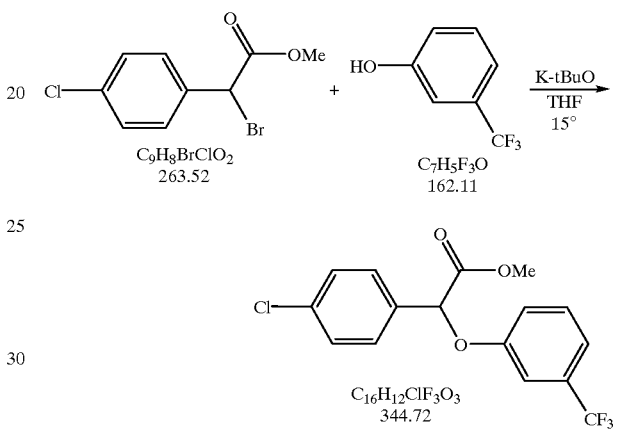

This step was similar to the same step in U.S. Pat. No. 3,517,050 with one exception, potassium t-butoxide was used in place of sodium methoxide to prevent generation of the corresponding methyl ether. A 5-L Morton reactor equipped with an overhead stirrer, a pot temperature detector, and addition funnel and under a nitrogen atmosphere was charged with methyl bromo-(4-chlorophenyl)-acetate (830 gm, 3.0 moles) and THF (600 ml). The reactor was cooled to 14°±3° C. in an ice-water bath and then a similarly cooled solution of trifluoromethyl-m-cresol (530 gm, 3.3 moles) in 1.0 M potassium t-butoxide in THF (3.1 L, 3.1 moles) was added. The reaction proceeded exothermically with a typical temperature rise exceeding 25° C. and the addition was controlled to maintain a temperature of 15°±2° C. and stirred at ambient temperature for 2 hours. HPLC was run on a Zorbax SB-C8 column at 30° C. measuring 250×4.6 mm and 5µ particle size. The mobile phase was 60:40 (v:v) acetonitrile: 0.1% $H_3PO_4$ at 1.5 ml/min. Detection was at 210 nm. The injected sample of 1 µl was dissolved in acetonitrile at a concentration of 10 mg/ml. The product had a retention time of 9.6 min., the starting ester eluted at 5.0 min., the phenol at 3.0 and the non-brominated ester at 3.8 min. The solvent was stripped using a rotary evaporator to obtain a yellow slush that was dissolved in a mixture of 4.0 L water and 12.0 L ether. The mixture was separated and the organic phase was washed once with 1.6 L 5% (w:w) aqueous NaOH followed by 1.6 L water and finally 1.6 L 25% (w:w) aqueous NaCl. The organic phase was dried over 0.32 kg $MgSO_4$ and filtered through Whatman #1 filter paper. The solvent was stripped to obtain 1.0 kg of damp, off-white crystals. This was recrystallized on the rotary evaporator by dissolving in 1.0 L methylcyclohexane at 75° C. and then cooling to 20° C.

The crystals were filtered through Whatman #1 filter paper and washed with three 0.25 L portions of cool (15° C.) methylcyclohexane. The wet product (0.97 kg) was dried overnight to obtain 0.81 kg of 98% pure product that corresponds to a 79% yield. The product proton NMR (CDCl$_3$, 300 MHz) shows shifts at 3.75 (s, 3H), 5.63 (s, 1H) and 7.05–7.55 (m, 8H).

Example 3

This example relates to the preparation of 4-Chlorophenyl-(3-trifluoromethylphenoxy)-acetic Acid

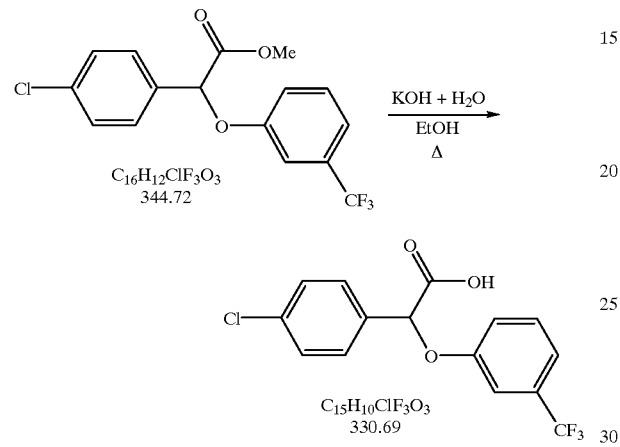

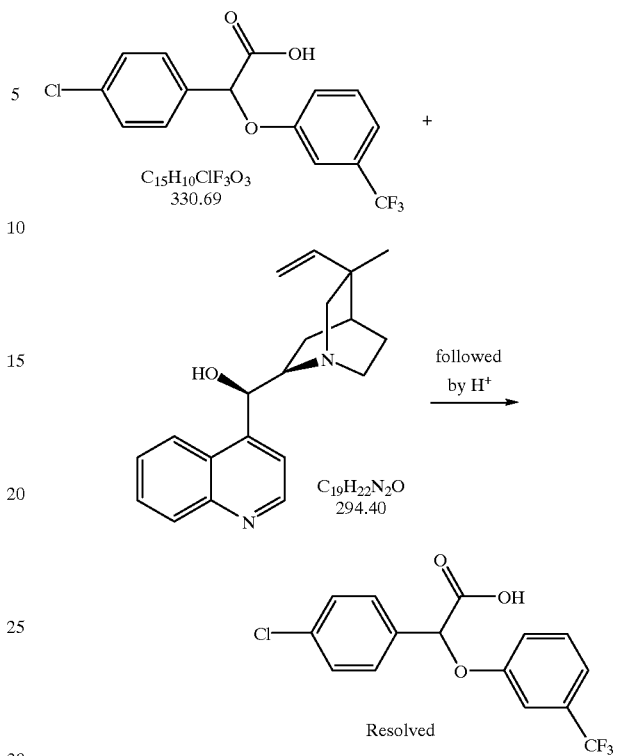

A 12-L Morton reactor with magnetic stirrer, pot temperature controller, a reflux condenser and under a nitrogen atmosphere was charged with methyl 4-chlorophenyl-(3-trifluoromethylphenoxy)-acetate (810 gm, 2.3 moles) and absolute ethanol (5.8 L) and heated with stirring to 57° C. to dissolve the solid. A solution of KOH (520 gm, 9.3 moles) in 0.98 L water was added. The solution was refluxed for 30 min. and solvent was stripped by a rotary evaporator to obtain 2.03 kg of a mixture of two nearly colorless liquids. These were dissolved in water (16 L) and treated with 16 gm neutral Norit, then filtered through a pad of infusorial earth retained on Whatman #1 filter paper. The pH of the filtrate was lowered from an initial range of 13 to a range of 1 to 2 by adding a total of 2.75 L of 3 M HCl (8.25 moles). A very sticky solid formed after the addition of the first 2.30 L of acid and ether (7 L) was added at this point. The two layers were separated and the organic layer was dried over MgSO$_4$ (230 gm) and filtered through Whatman #1 filter paper. The solvent was then stripped to obtain 0.85 kg water-white syrup. The material was then recrystallized on the rotary evaporator by adding methylcyclohexane (800 ml) and cooling to 18° C. with slow rotation. The temperature was then dropped to 5° C., the crystals were filtered, and washed 5 times with 0.10 L portions of cold (0° C.) methylcyclohexane to obtain 0.59 kg wet crystals. The wet crystals were dried to obtain 0.48 kg (62% yield) product with no p-chlorophenylacetic acid detectable in the proton NMR. The product proton NMR (CDCl$_3$, 300 MHz) shows shifts at 5.65 (s, 1H), 7.02–7.58 (m, 8H) and 10.6 (s, 1H).

Example 4

This example relates to the preparation of resolved enantiomers of 4-Chlorophenyl-(3-trifluoromethylphenoxy)-acetic Acid.

A 12-L open-top Morton reactor with an overhead stirrer was charged with 4-chlorophenyl-(3-trifluoromethylphenoxy)-acetic acid (350 gm, 1.06 moles) and isopropanol (4.0 L) and heated to 65°±3° C. A slurry of (−) cinchonidine (300 gm, 1.02 moles) in isopropanol (2.0 L) was added, rinsing all solid into the reactor with an additional 0.8 L of isopropanol. The temperature dropped from 65° to 56° C. and a transparent, orange solution ultimately formed and the mixture was held at 55°±5° C. for 2 hours. Fine crystals were collected by filtration through Whatman #1 filter paper, washing once with 0.7 L hot (55° C.) isopropanol. The crystals were dried for 16 hours at ambient temperature in a 12.6-L vacuum oven under a 5 LPM nitrogen flow. The dry solid weighed 0.37 kg and had an 80% enantiomeric excess (ee) of the (+) enantiomer. The enantiomeric excess was determined by HPLC using a 250×4.6 mm R,R-WhelkO-1 column at ambient temperature. Injected samples were 20 μl of 2 mg/ml solutions of the samples in ethanol. The column was eluted with 95:5:0.4, hexane:isopropanol:acetic acid at a flow of 1 ml/min. Detection was at 210 nm. The (+) enantiomer eluted at 7 to 8 min. and the (−) enantiomer at 11 to 13 min. The mother liquor dropped a second crop almost immediately that was filtered, washed, and dried to afford 0.06 kg salt that has a 90% ee of the (−)-enantiomer. Similarly third, fourth and fifth crops weighing 0.03 kg, 0.03 kg and 0.7 kg, respectively, were obtained; with (−) enantiomer excesses of 88%, 89% and 92%, respectively.

The crude (+) salt (320 gm) was recrystallized from a mixture of ethanol (5.9 L) methanol (1.2 L). The mixture was heated with overhead stirring to dissolve, cooled at ambient temperature for 16 hours, filtered and washed twice with 0.20 L of 5:1 (v:v) ethanol:methanol. The crystals were dried to obtain 0.24 kg of the (+) enantiomer that had an ee of 97%. This corresponded to an 80% recovery of this isomer. The resolved salt was suspended in a mixture of ether (6.5 L) and water (4.0 L) with overhead stirring. The pH was lowered to 0–1 as measured by pH indicating strips with a solution of concentrated H₂SO₄ (0.13 L) in water (2.5 L). The phases were separated and the organic phase and washed twice with 6.5 L portions of water. Ether (1.9 L) was added and the organic layer washed once more with 6.5 L water. After the final separation, 0.1 L of 25% (w:w) aqueous NaCl was added clean up any slight emulsion. The product was dried over 0.19 kg MgSO₄, filtered and solvent removed solvent to obtain 0.13 kg of water-white syrup that solidifies on cooling. This corresponded to a 97% recovery of product that had a 95% ee of the (+) enantiomer. $[\alpha]_D$+5.814° (c.=0.069 in methyl alcohol).

The combined, crude (−) salt (200 gm) was recrystallized from isopropanol (3.1 L). The mixture was heated to dissolve almost all of the solid and fast-filtered to remove insoluble solids. The mixture was then cooled with stirring at ambient temperature for 16 hours, filtered, washed, and dried to obtain 0.16 kg of the (−) enantiomer that has an ee of 97%. This corresponds to a 49% recovery of this isomer. The (−) enantiomer of the acid was isolated in the same manner as described above for the (+) acid. The resolved salt was suspended in ether and water, the pH lowered with concentrated H₂SO₄, and the product extracted in the organic phase.

Example 5

A. Preparation of (−) 4-Chlorophenyl-(3-trifluoromethylphenoxy)-acetyl Chloride

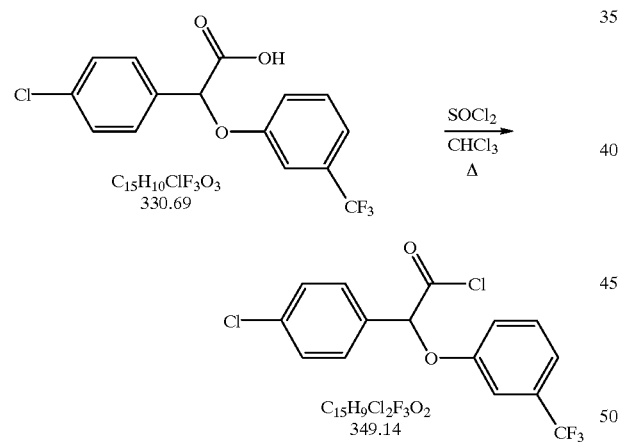

A 2-L evaporation flask with magnetic stirrer, Claissen adapter, pot thermometer and a reflux condenser routed to a gas scrubber was charged with (−) 4-chlorophenyl-(3-trifluoromethylphenoxy)-acetic acid (143 g, 0.42 mole based on 97% purity) and CHCl₃ (170 ml) and heated to boiling in order to dissolve. SOCl₂ (38 ml, 62.1 gm, 0.52 mole) was added. The mixture was heated to reflux (68° C. final) for 4.5 hours and then stripped of volatiles to obtain 151 g yellow, turbid liquid (103% apparent yield). The material was used in the next step without further purification.

B. Preparation of (+) 4-Chlorophenyl-(3-trifluoromethylphenoxy)-acetyl Chloride

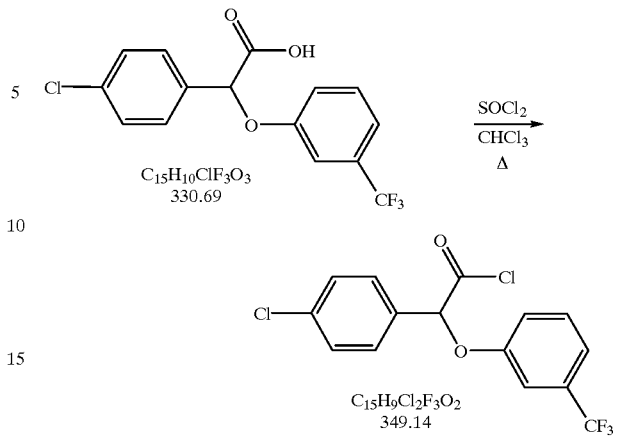

A 3-L evaporation flask with magnetic stirrer, Claissen adapter, pot thermometer and a reflux condenser routed to a gas scrubber was charged with (+) 4-chlorophenyl-(3-trifluoromethylphenoxy)-acetic acid (131 g, 0.37 mole) and CHCl₃ (152 ml) and heated to boiling in order to dissolve. SOCl₂ (35 ml, 56.5 g, 0.48 mole) was added. The mixture was heated to reflux (70° C. final) for 4 hours and then stripped of volatiles to obtain 139 g liquid. The material was used in the next step without further purification.

Example 6

A. Preparation of (−)2-Acetamidoethyl 4-Chlorophenyl-(3-trifluoromethylphenoxy)-acetate

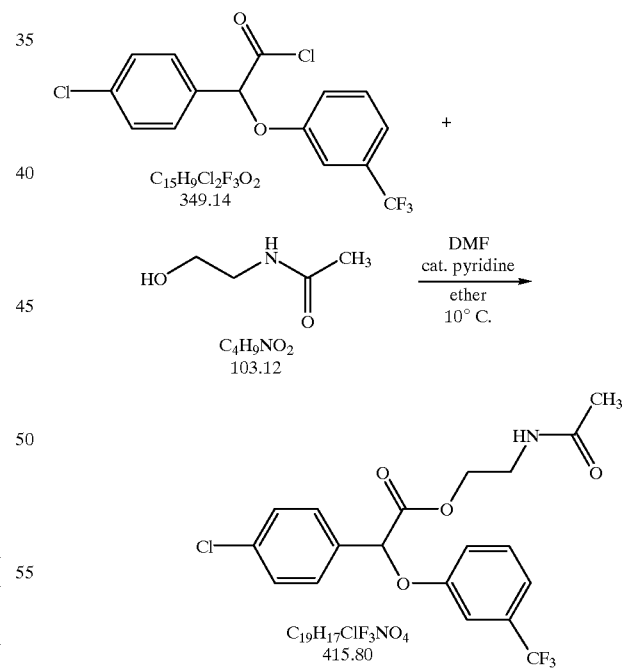

A 3-L round-bottom flask with magnetic stirrer, pot thermometer, under a nitrogen atmosphere and in an ice-water bath was charged with DMF (420 ml), pyridine (37 ml, 36 g, 0.46 mole) and N-acetoethanolamine (39 ml, 43 g, 0.42 mole). The mixture was cooled to 0° to 5° C. and a solution of crude (−) 4-chlorophenyl-(3-trifluoromethylphenoxy)-acetyl chloride (151 gm, 0.42 mole based on 100% yield of previous step) in ether (170 ml) was added over a 40 min. period so as to maintain the pot temperature below 13° C. The mixture was stirred at ambient temperature for 16 hours and dissolved by adding water (960 ml) followed by ethyl acetate (630 ml). The water addition proceeded exothermically raising the temperature from 24° to 34° C. Ethyl acetate addition caused a temperature drop to 30° C. The layers were separated and the aqueous phase extracted once with ethyl acetate (125 ml). The combined organic layers were extracted once with 7% (w:w) aqueous NaHCO$_3$ (125 ml) and five times with 60 ml portions of water and then twice with 60 ml portions of 25% (w:w) aqueous NaCl. The product was dried over MgSO$_4$ (42 g) and filtered through Whatman #1 filter paper. Solvent was stripped using a rotary evaporator to obtain 160 g of a yellow syrup corresponding to an 80% yield based on the proton nmr that shows 87% product, 8% EtOAc, 4% non-brominated amide, and 1% DMF. This syrup was dissolved in MTBE (225 ml) at ambient temperature and chilled (−15° C.) 85% hexanes (400 ml) was added with stirring. Two liquids formed, then crystals, then the mixture formed a solid. The solid mass was scraped onto a Buchner funnel fitted with Whatman #1, packed down and washed three times with 100 ml portions of 1:1 (v:v) MTBE:hexanes to obtain 312 g wet product which dries to 127 gm, corresponding to a 73% yield.

B. Preparation of (+) 2-Acetamidoethyl 4-Chlorophenyl-(3-trifluoromethylphenoxy)-acetate

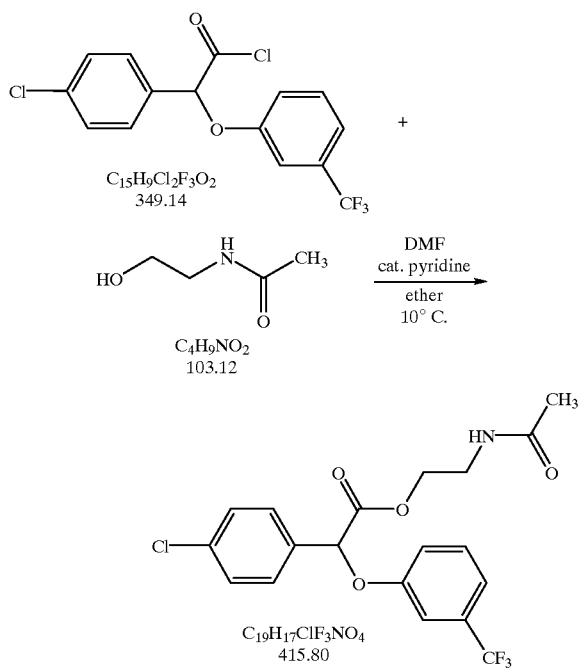

A 3-L round-bottom flask with magnetic stirrer, pot thermometer, under a nitrogen atmosphere and in an ice-water bath was charged with DMF (365 ml), pyridine (33 ml, 32.3 g, 0.41 mole) and N-acetoethanolamine (34 ml, 38.1 g, 0.37 mole). The mixture was cooled to 0° to 5° C. and a solution of crude (+) 4-chlorophenyl-(3-trifluoromethylphenoxy)-acetyl chloride (139 gm, 0.37 mole based on 100% yield of previous step) in ether (155 ml) was added over a 25 min. period so as to maintain the pot temperature below 13° C. The mixture was stirred at ambient temperature 40 hours and dissolved by adding water (850 ml) followed by ethyl acetate (550 ml). The water addition proceeded exothermically raising the temperature from 24° to 34° C. Ethyl acetate addition caused a temperature drop to 30° C. The layers were separated and the aqueous phase extracted once with ethyl acetate (110 ml). The combined organic layers were washed twice with 55 ml portions of water and then five times with 55 ml portions of 25% (w:w) aqueous NaCl and dried over 30 g MgSO$_4$ and filtered through Whatman #1 filter paper. Solvent was stripped using a rotary evaporator to obtain 168 g yellow liquid corresponding to an 86% yield based on the proton nmr that shows 79% product, 9% EtOAc, 8% non-brominated amide, and 4% DMF. The product was crystallized in an 800-ml beaker by dissolving in MTBE (200 ml) at ambient temperature, cooling at −15° for 1.4 hours, adding 200 ml 85% hexanes and then chilling 1 hour. The solid mass was scraped out onto a Buchner funnel fitted with Whatman #1, packed down and washed once with 1:1 (v:v) MTBE:hexanes (100 ml) to obtain 201 gm wet product. The product was dried under nitrogen flow and triturated with 85% hexanes (700 ml) using an overhead stirrer. The material was filtered and dried to obtain 87 gm product. $[\alpha]_D$ +2.769° (c.=0.048 in methyl alcohol). $[\alpha]_D$ −2.716° (c.= 0.049 in methyl alcohol). The (+) and (−) enantiomers were also analyzed by HPLC using a 250×4.6 mm R,R-WhelkO-1 column at ambient temperature. Injected samples were 20 $\mu$l of 2 mg/ml solutions of the samples in ethanol. The column was eluted with 60:40, isopropanol:hexane at a flow of 1 ml/min. Detection was at 220 nm. The (+) enantiomer eluted at 5.0 to 5.2 min. and the (−) enantiomer at 5.7 to 5.9 min.

Example 7

This example relates to the inhibition of cytochrome P450 2C9(CYP2C9) by the compounds of the present invention.

Tolbutamide hydroxylation activity (100 $\mu$M $^{14}$C-tolbutamide; 1 mM NADPH) was assayed in pooled human liver microsomes (0.6 mg protein/ml)) for 60 minutes at 37° C. both with and without test compounds. Racemic halofenic acid, (−) halofenic acid and (+) halofenic acid were tested (0.25 $\mu$M to 40 $\mu$M). As shown in FIG. 1, racemic halofenic acid inhibited CYP2C9-mediated tolbutamide hydroxylation activity in human liver microsomes with an apparent IC$_{50}$ of 0.45 $\mu$M. A substantial difference was noted in the ability of the enantiomers of halofenic acid to inhibit CYP2C9. The (+) halofenic acid had an apparent IC$_{50}$ of 0.22 $\mu$M whereas the (−) halofenic acid was almost 20-fold less potent with an apparent IC$_{50}$ of 3.6 $\mu$M.

Example 8

This example relates to the time course of glucose-lowering for the compounds of the present invention.

A. Material and Methods

Male, 9–10 weeks old, C57BL/6J ob/ob mice were purchased from The Jackson Laboratory (Bar Harbor, Me., USA). Animals were housed (4–5 mice/cage) under standard laboratory conditions at 22° C. and 50% relative humidity, and were maintained on a diet of Purina rodent chow and water ad libitum. Prior to treatment, blood was collected from the tail vein of each animal. Mice that had non-fasting plasma glucose levels between 300 and 500 mg/dl were used. Each treatment group consisted of 10 mice that were distributed so that the mean glucose levels were equivalent in each group at the start of the study. Mice were dosed orally once by gavage with either vehicle, racemic halofenate (250 mg/kg), (−) halofenate (250 mg/kg) or (+) halofenate (250 mg/kg). All compounds were delivered in a liquid formulation contained 5% (v/v) dimethyl sulfoxide (DMSO), 1% (v/v) tween 80 and 2.7% (w/v) methylcellulose. The gavage volume was 10 ml/kg. Blood samples were taken at 1.5, 3, 4.5, 6, 7.5, 9 and 24 hour after the dose and analyzed for plasma glucose. Plasma glucose concentrations were determined colorimetrically using glucose oxidase method (Sigma Chemical Co, St. Louis, Mo., USA). Significance difference between groups (comparing drug-treated to vehicle-treated or between drug-treated groups) was evaluated using Student unpaired t-test.

B. Results

Figure 2:
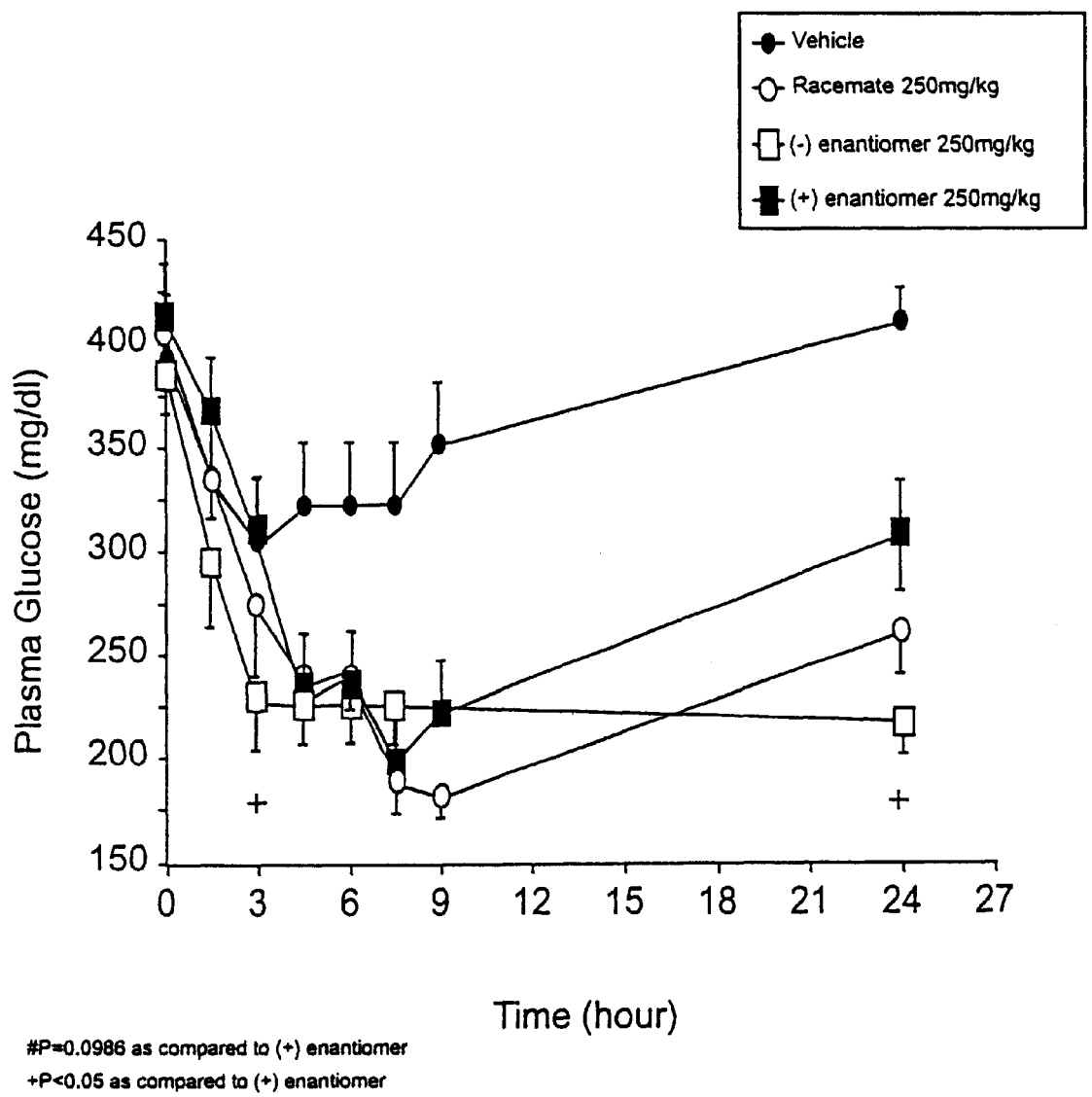
FIG. 2 shows the time course of glucose-lowering following a single oral dose of racemic halofenate, (−) enantiomer of halofenate or (+) enantiomer of halofenate at 250 mg/kg in diabetic ob/ob mice. The (−) enantiomer showed the most rapid onset of action and the longest duration of action. The decrease in glucose was significant (p<0.05) for the (−) enantiomer compared to control for all points from 3 to 24 hours. Racemic halofenate and the (+) enantiomer were also significant (p<0.05) for all points from 4.5 to 24 hours. The plasma glucose at 24 hours was 217±16.4 mg/dl in animals treated with the (−) enantiomer, compared to 306±28.5 mg/dl and 259.3±20.8 mg/dl for animals treated with the (+) enantiomer and the racemate, respectively. The plasma glucose in the vehicle treated controls was 408±16.2 mg/dl at 24 hours. The (−) enantiomer was more effective and significantly different (p<0.05) from the (+) enantiomer at both the 3 hour and 24 hour time points.

As illustrated in FIG. 2, racemic halofenate significantly reduced plasma glucose concentrations at most of the timepoints with the peak activity at 9 hours. (−) Halofenate showed a plasma glucose reduction as early as 1.5 hours and reached its peak activity at 3 hours. The plasma glucose concentrations remained low up to 24 hours. (+) Halofenate did not show significant activity until 4.5 hours and the peak activity was at 7.5 hours. Plasma glucose started to rebound afterward. There were significant differences between (−) and (+) enantiomers of halofenate at the 3 and 24-hour timepoints. The activity of the (−) halofenate was more rapid onset and sustained longer.

Example 9

This example relates to the Glucose lowering activity of the compounds of the present invention.

A. Materials and Methods

Male, 8–9 weeks old, C57BL/6J ob/ob mice were purchased from The Jackson Laboratory (Bar Harbor, Me., USA). Animals were housed (4–5 mice/cage) under standard laboratory conditions at 22° C. and 50% relative humidity, and were maintained on a diet of Purina rodent chow and water ad libitum. Prior to treatment, blood was collected from the tail vein of each animal. Mice that had non-fasting plasma glucose levels between 300 and 520 mg/dL were used. Each treatment group consisted of 10 mice that were distributed so that the mean glucose levels were equivalent in each group as the start of the study. Mice were dosed orally by gavage once a day for 5 days with either vehicle, racemic halofenate (250 mg/kg), (−) halofenate (125 and 250 mg/kg) or (+) halofenate (125 and 250 mg/kg). Racemic halofenate was delivered in 2.7% (w/v) methylcellulose and both the (−) enantiomer and (+) enantiomer were delivered in a liquid formulation contained 5% (v/v) dimethyl sulfoxide (DMSO), 1% (v/v) tween 80 and 2.7% (w/v) methylcellulose. The gavage volume was 10 ml/kg. Blood samples were taken at 3, 6, 27, 30 and 120 hour after the first dose and analyzed for plasma glucose and insulin. The animals were fasted overnight (14 hours) before the 120 hours sampling. Plasma glucose concentrations were determined colorimetrically using glucose oxidase method (Sigma Chemical Co, St. Louis, Mo., USA). Plasma insulin concentrations were determined by using the Rat Insulin RIA Kit from Linco Research Inc. (St. Charles, Mo., USA). Significance difference between groups (comparing drug-treated to vehicle-treated) was evaluated using Student unpaired t-test.

B. Results

Figure 3:
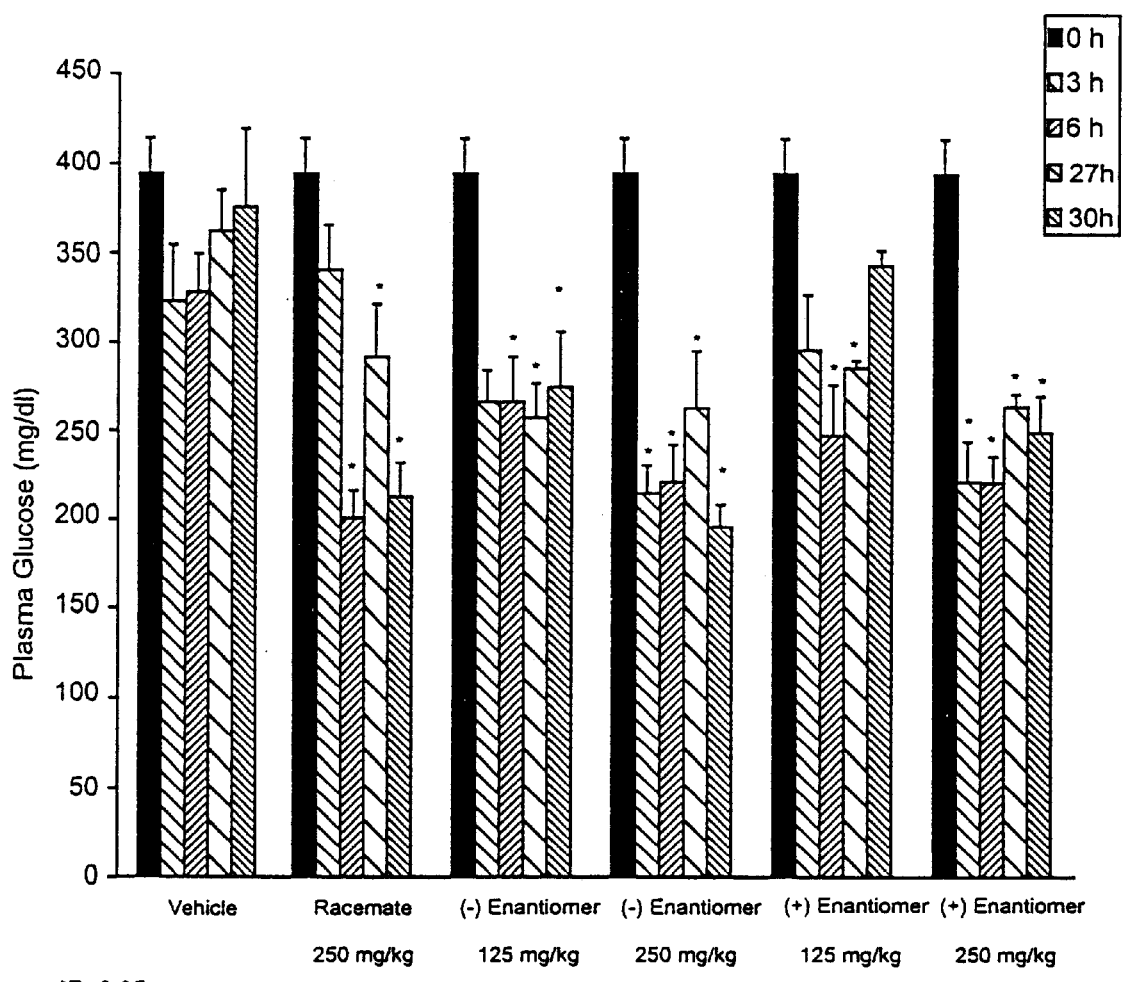
FIG. 3 shows the ability of racemic halofenate and both the (−) and (+) enantiomers of halofenate to lower plasma glucose in diabetic ob/ob mice following daily oral administration. The racemate was given at a dose of 250 mg/kg/day and the enantiomers were given at doses of 125 mg/kg/day and 250 mg/kg/day. Significant decreases in glucose levels relative to control animals were observed in animals treated with racemic halofenate and both the (−) and (+) enantiomers. At the low dose (125 mg/kg) of treatment with the (−) and (+) enantiomers, the (−) enantiomer was significant at 6, 27 and 30 hours whereas the (+) enantiomer was significant at only 6 and 27 hours.
Figure 4:
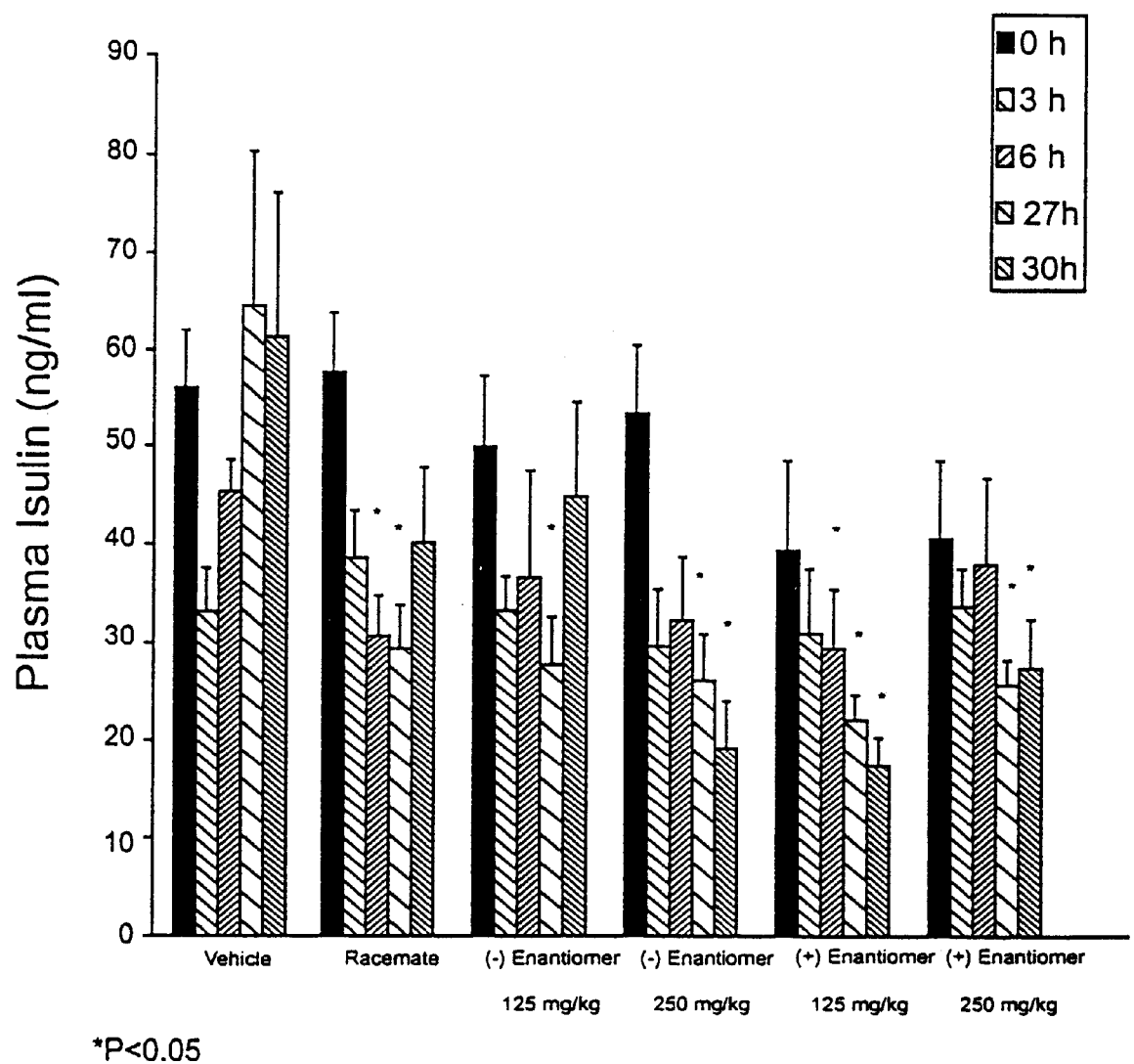
FIG. 4 shows the plasma insulin levels in the ob/ob mice treated with racemic halofenate and both the (−) and (+) enantiomers of halofenate in diabetic ob/ob mice following daily oral administration. The racemate was given at a dose of 250 mg/kg/day and the enantiomers were given at doses of 125 mg/kg/day and 250 mg/kg/day. Relative to the vehicle control, insulins were lower in the animals treated with either the racemate or either of the enantiomers of halofenate. At the high dose, the greatest extent of reduced plasma insulin was noted at 27 and 30 hours in animals treated with both the (−) and (+) enantiomers of halofenate following two days of treatment.
Figure 5:
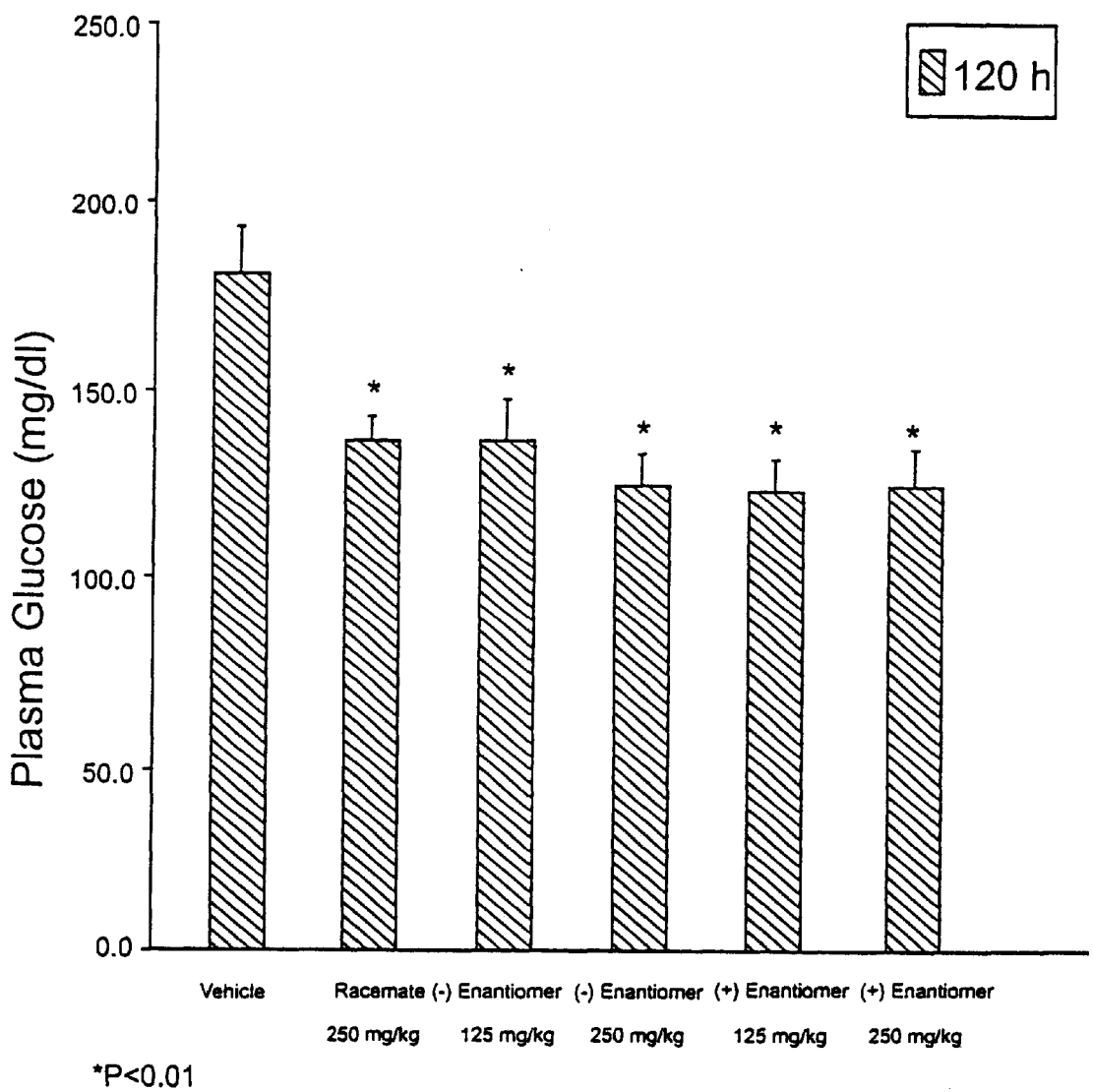
FIG. 5 shows plasma glucose levels following an overnight fast in ob/ob mice after 5 days treatment with vehicle, racemic halofenate at 250 mg/kg/day, (−) enantiomer of halofenate at 125 mg/kg/day and 250 mg/kg/day or (+) enantiomer of halofenate at 125 mg/kg/day or 250 mg/kg/day. The control animals were hyperglycemic with plasma glucose levels of 185.4±12.3 mg/dl. All of the animals treated with halofenate showed significant (p<0.01) reductions in glucose. The high doses of both enantiomers lowered the glucose to near normal levels at 127.3±8.0 mg/dl and 127.2±9.7 mg/dl for the (−) enantiomer and (+) enantiomer treated animals, respectively.
Figure 6:
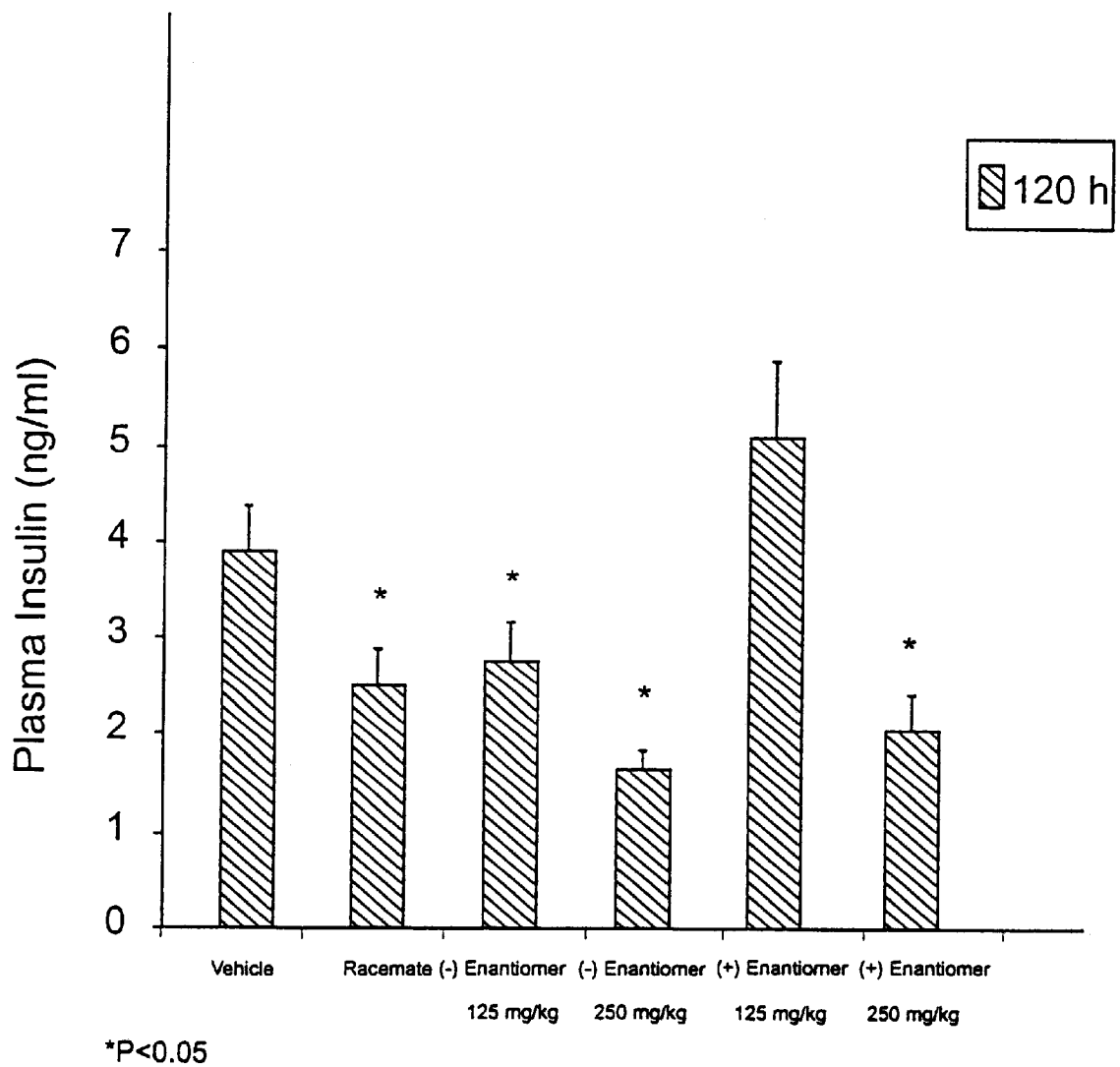
FIG. 6 shows the overnight fasting plasma insulin levels in the ob/ob mice treated with vehicle, racemic halofenate at 250 mg/kg/day, (−) enantiomer at 125 mg/kg/day and 250 mg/kg/day or (+) enantiomer of halofenate at 125 mg/kg/day or 250 mg/kg/day for 5 days. Significantly lower plasma insulins were observed in animals receiving both doses of (−) enantiomer. The low dose of (+) enantiomer of halofenate did not lower plasma insulin, although the high dose of the (+) enantiomer resulted in a decrease in plasma insulin.

As illustrated in FIG. 3, (−) halofenate significantly reduced plasma glucose concentrations at 6, 27 and 30 hours. (−) Halofenate at both dosage levels significantly lowered plasma glucose concentrations at 6, 27 and 30 hours. The high-dose (250 mg/kg) was also active at 3 hours. (+) Halofenate at 125 mg/kg showed plasma glucose reduction at 6 and 27 hours, where at 250 mg/kg, lowered plasma glucose concentrations were observed at 3, 6, 27 and 30 hours. Plasma insulin levels are shown in FIG. 4. Racemic halofenate significantly reduced insulin at 6 and 27 hours. Plasma insulins were significantly reduced in the (−) halofenate group at 27 hours at both doses and was significantly reduced at 30 hours in the animals treated with 250 mg/kg/day. (+) halofenate significantly reduced insulin at 27 and 30 hours at both doses. At 125 mg/kg/day a significant reduction was also observed after 6 hours. After fasting overnight (at 120 hours), all treatments reduced plasma glucose concentrations significantly (FIG. 5). Plasma insulins were significantly reduced in all halofenate treated groups except the (+) halofenate at 125 mg/kg/day (FIG. 6).

Example 10

This example relates to the improvement in Insulin Resistance and Impaired Glucose Tolerance for the compounds of the present invention.

A. Materials and Methods

Male, 8–9 weeks old Zucker fa/fa rats (Charles River, ) were housed (2–3 rats/cage) under standard laboratory conditions at 22° C. and 50% relative humidity, and were maintained on a diet of Purina rodent chow and water ad libitum. Prior to treatment, rats were assigned to 6 groups based on body weight. Each treatment group consisted of 8 rats. Rats were dosed orally once by gavage with either vehicle, racemic halofenate (100 mg/kg), (−) halofenate (50 or 100 mg/kg) or (+) halofenate (50 or 100 mg/kg). All compounds were delivered in a liquid formulation contained 5% (v/v) dimethyl sulfoxide (DMSO), 1% (v/v) tween 80 and 2.7% (w/v) methylcellulose. The gavage volume was 10 ml/kg. All rats received an oral glucose challenge (1.9 g/kg) 5.5 hours after the treatment and 4 hours after withdrawal of the food. Blood samples were taken at 0, 15, 30, 60, 90, 120, and 180 minutes following the glucose challenge for plasma glucose measurement. The vehicle, (−) halofenate (50 mg/kg) and (+) halofenate (50 mg/kg) groups were subjected to an insulin challenge following daily gavage of the respective treatments for 5 days. On day 5, rats received the intravenous insulin (0.75 U/kg) 5.5 hours after the last dose and 4 hours after withdrawal of the food. Blood samples were taken at 3, 6, 9, 12, 15 and 18 minutes following the insulin injection for plasma glucose measurement. Plasma glucose concentrations were determined colorimetrically using glucose oxidase method (Sigma Chemical Co, St. Louis, Mo., U.S.A.). Significance difference between groups (comparing drug-treated to vehicle-treated or between drug-treated groups) was evaluated using Student unpaired t-test.

B. Results

Figure 7A:
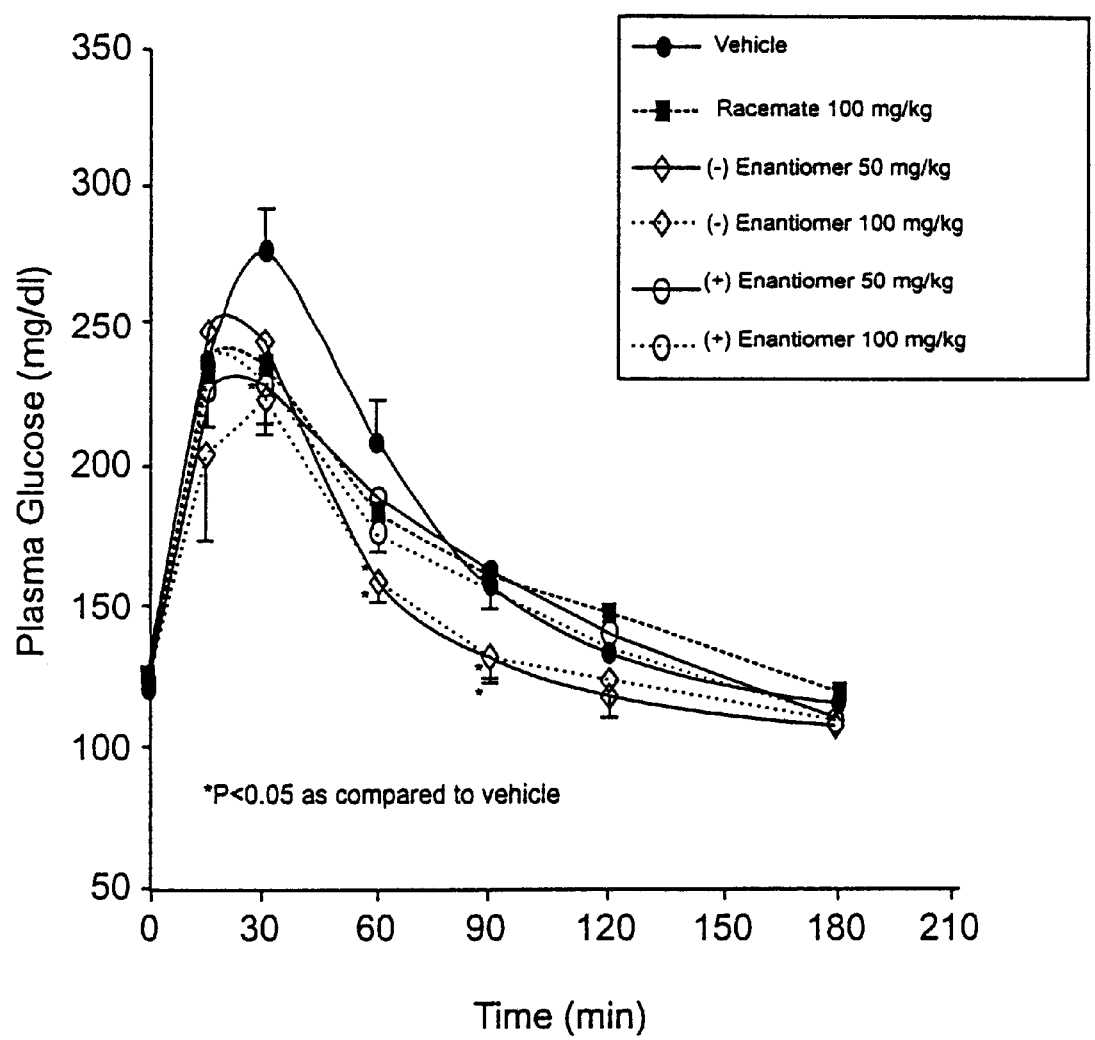
FIG. 7A shows plasma glucose levels following an oral glucose challenge in Zucker fatty rats, a model of insulin resistance and Impaired Glucose Tolerance. These animals were treated with either a vehicle control, racemic halofenate, (−) halofenate or (+) halofenate 5.5 hours prior to the glucose challenge. The racemate was given at 100 mg/kg and both of the enantiomers were given at 50 and 100 mg/kg. In the control animals the glucose rose to >250 mg/dl 30 minutes after the challenge, a clear indication of impaired glucose tolerance. The plasma glucose was reduced in rats that had received racemic halofenate, especially between 30–60 minutes after the challenge. Animals that received the (−) halofenate at 100 mg/kg had the greatest degree of glucose-lowering of all the treated animals. Animals treated with the (−) halofenate had lower glucose levels that persisted at 90–120 minutes, compared to those rats treated with the racemate or (+) halofenate.
Figure 7B:
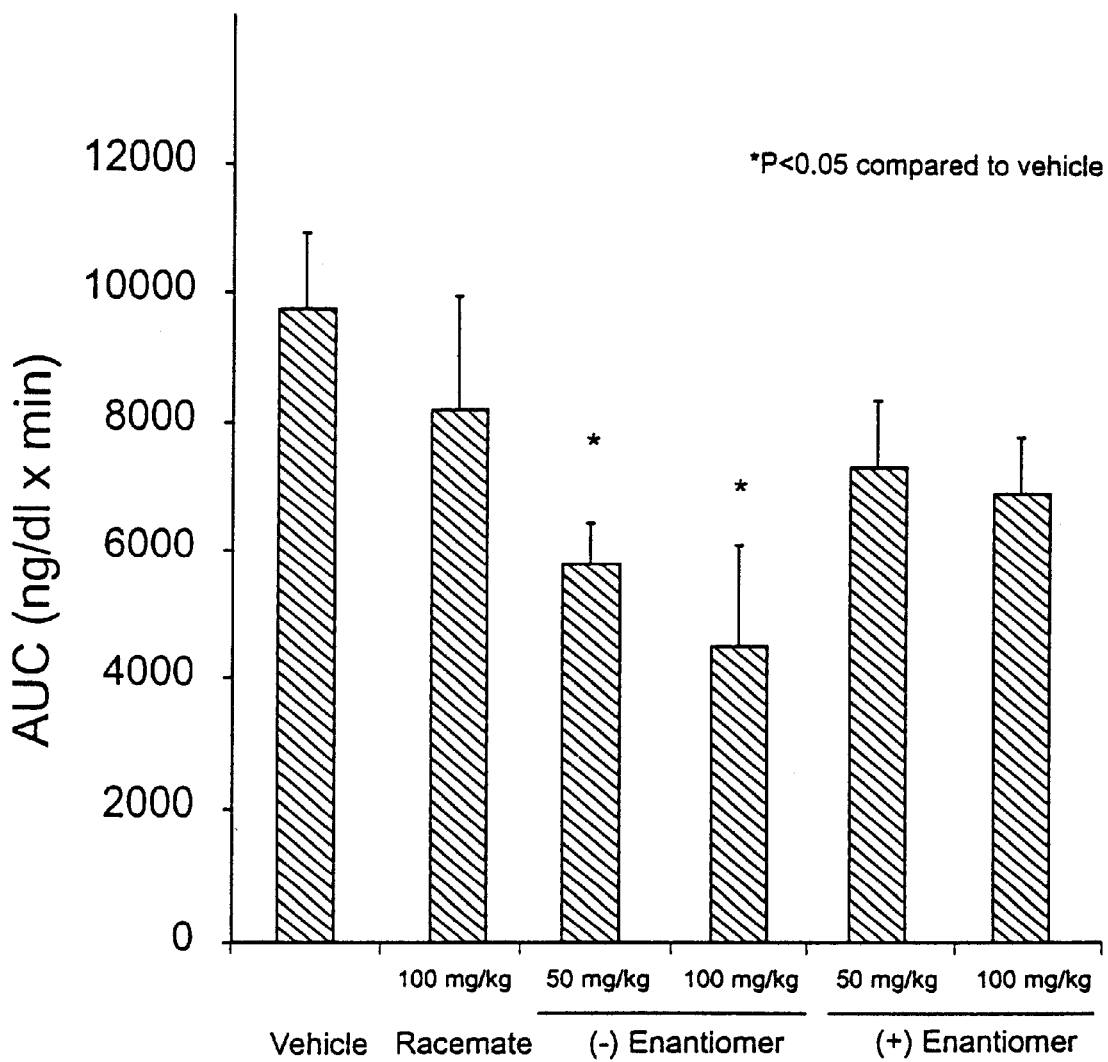
FIG. 7B compares the incremental area under the curve (AUC) for the animals in each group. Significant changes (p<0.05) were noted in the groups treated with both doses of the (−) halofenate. Although the AUC was lower in the other groups relative to the control, the changes were not significant.

As illustrated in FIG. 7A, Zucker fatty rats with Impaired Glucose Tolerance had lower plasma glucose levels after a glucose challenge following treatment with halofenate. The (−) halofenate was the most effective in lowering the glucose and had an effect that persisted longer than the racemate or (+) enantiomer. FIG. 7B shows the incremental area under the curve (AUC) for all the treatment groups. The animals treated with the (−) halofenate showed significant reductions in the glucose area relative to vehicle-treated controls. Although the AUC was decreased in the groups treated with the racemate or (+) halofenate, the effects were not as great as in the (−) halofenate-treated rats and the differences were not statistically significant.

Figure 8:
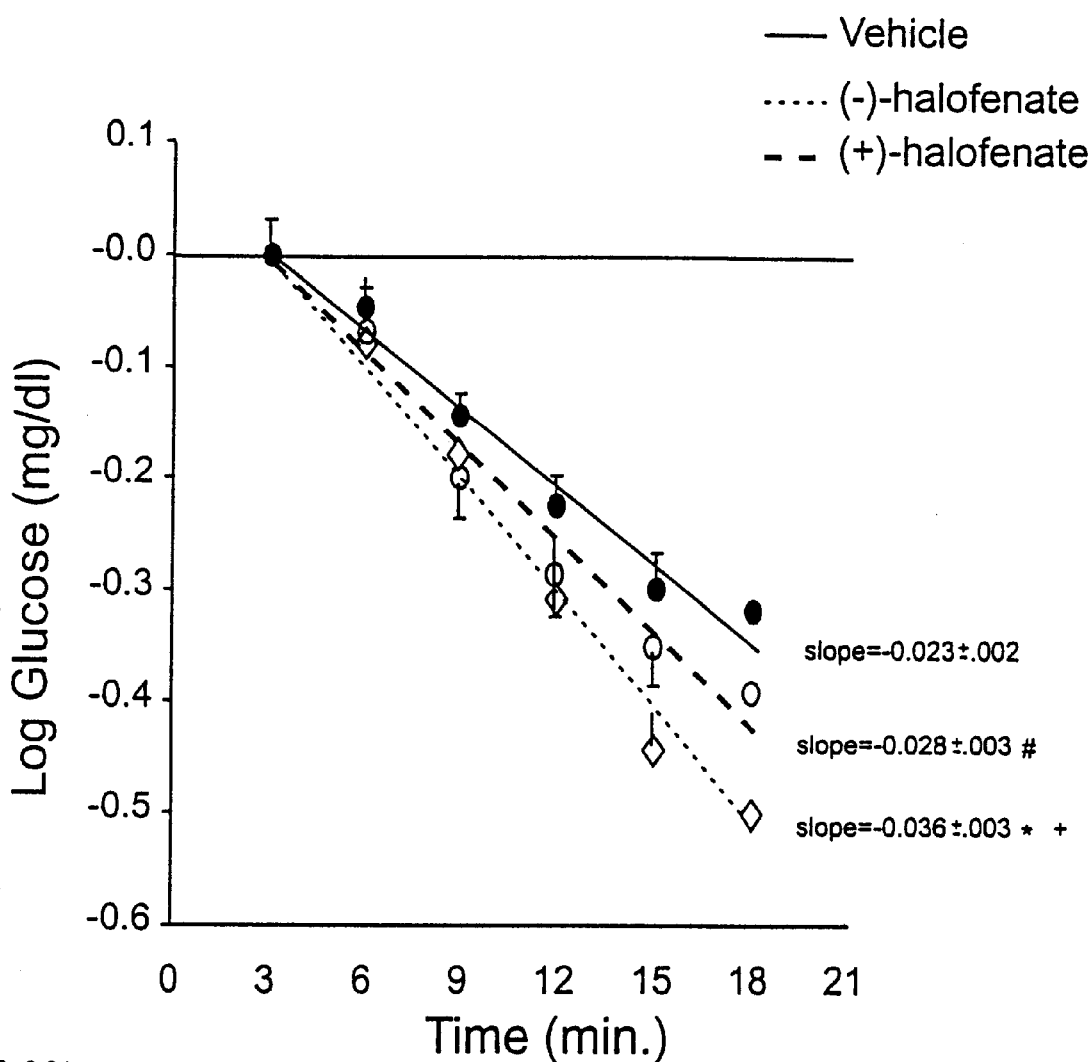
FIG. 8 shows the results of a short insulin tolerance test in Zucker fatty rats that were treated with either a vehicle control, (−) halofenate (50 mg/kg/day) or (+) halofenate (50 mg/kg/day) for 5 days. This test is a measure of the insulin sensitivity of the test animals, the slope of the decline in glucose representing a direct measure of insulin responsiveness. The (−) halofenate-treated animals were significantly more insulin sensitive than the vehicle-treated (p<0.01) or the (+) halofenate-treated (p<0.05) animals.

Changes in insulin sensitivity were assessed by monitoring the fall in glucose after an intravenous injection of insulin. The slope of the line is a direct indication of the insulin sensitivity of the test animal. As shown in FIG. 8, the insulin sensitivity was improved significantly after 5 days of treatment with (−) halofenate compared to the vehicle-treated controls (p<0.01) and animals treated with (+) halofenate (p<0.05). Treatment with (+) halofenate had a small effect on insulin sensitivity that was not significantly different from the vehicle-treated control (p=0.083). Treatment with (−) halofenate substantially reduced the insulin resistance in the Zucker fatty rat, a well-established model of Impaired Glucose Tolerance and insulin resistance.

Example 11

This example relates to the lipid lowering activity of the compounds of the present invention.

A. Materials and methods

Male Zucker diabetic fatty (ZDF) rats were obtained from GMI Laboratories (Indianapolis, Ind.) at 9 weeks of age. Vehicle or enantiomers of halofenate administered by oral gavage on a daily basis starting at 74 days of age. Initial blood samples were obtained for analysis one day before treatment and at the indicated times in the treatment protocol. Blood was analyzed for plasma triglyceride and cholesterol by standard techniques.

B. Results

Figure 9A:
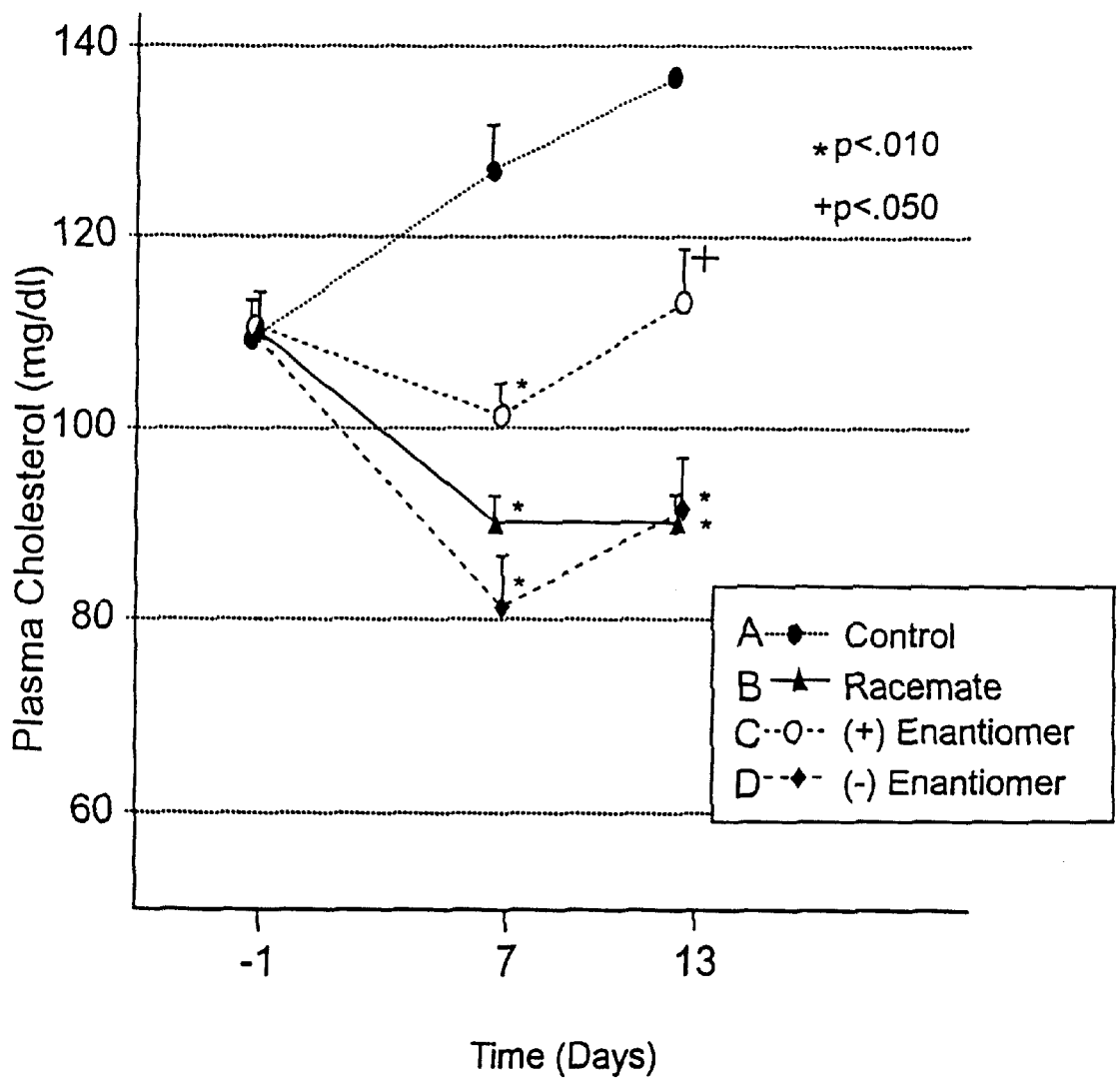
FIG. 9A shows plasma cholesterol levels in Zucker Diabetic Fatty rats treated for 13 days with racemic halofenate, (−) enantiomer or (+) enantiomer at 50 mg/kg/day, 25 mg/kg/day or 25 mg/kg/day, respectively, relative to a vehicle treated control group. In both the (−) enantiomer and racemate treated animals, the plasma cholesterol declined with treatment. The cholesterol in the (+) enantiomer treated animals remained relatively constant, whereas cholesterol rose in the control animals.
Figure 9B:
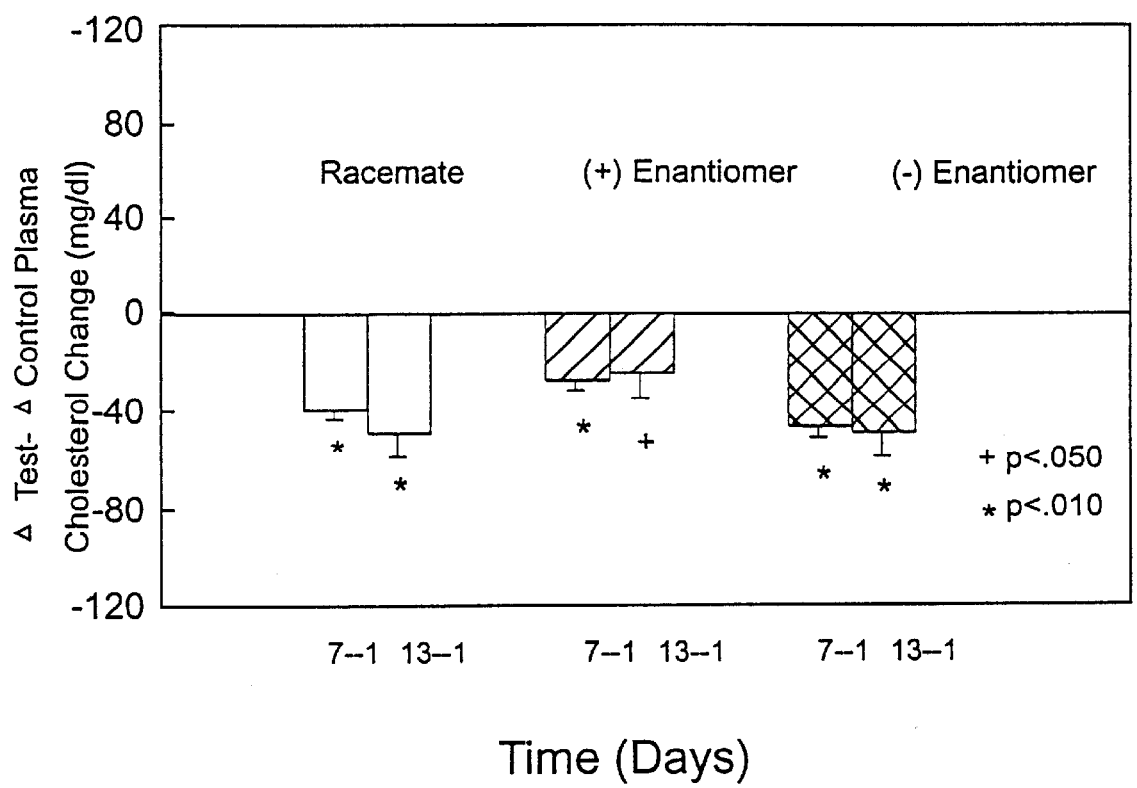
FIG. 9B compares the differences in plasma cholesterol between the control group and the treated groups. The (−) enantiomer was the most active of the species tested.
Figure 10A:
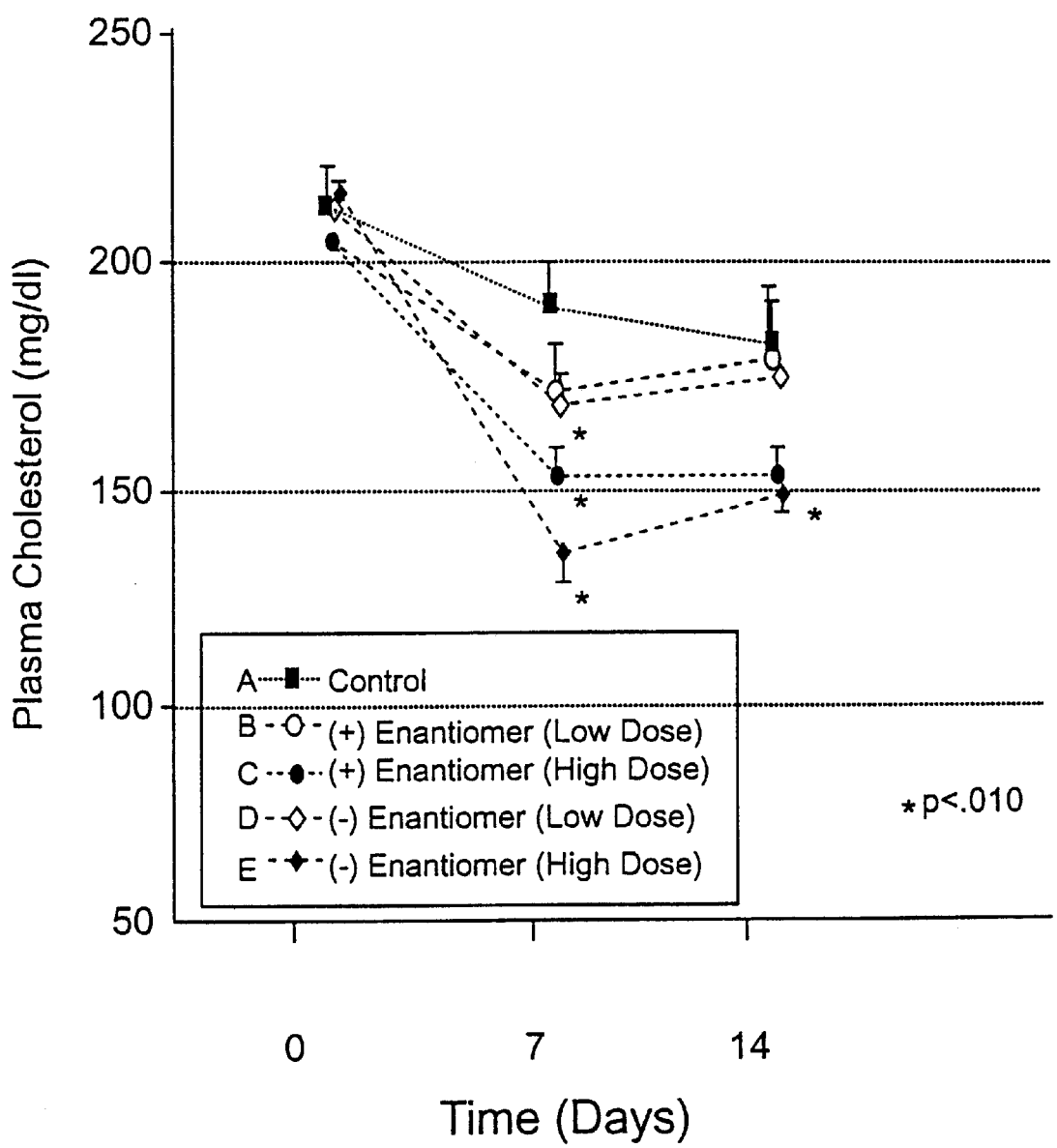
FIG. 10A shows plasma cholesterol levels in Zucker Diabetic Fatty rats treated for 14 days with either (−) enantiomer or (+) enantiomer of halofenate at either 12.5 mg/kg/day (Low dose) or 37.5 mg/kg/day (High dose)
Figure 10B:
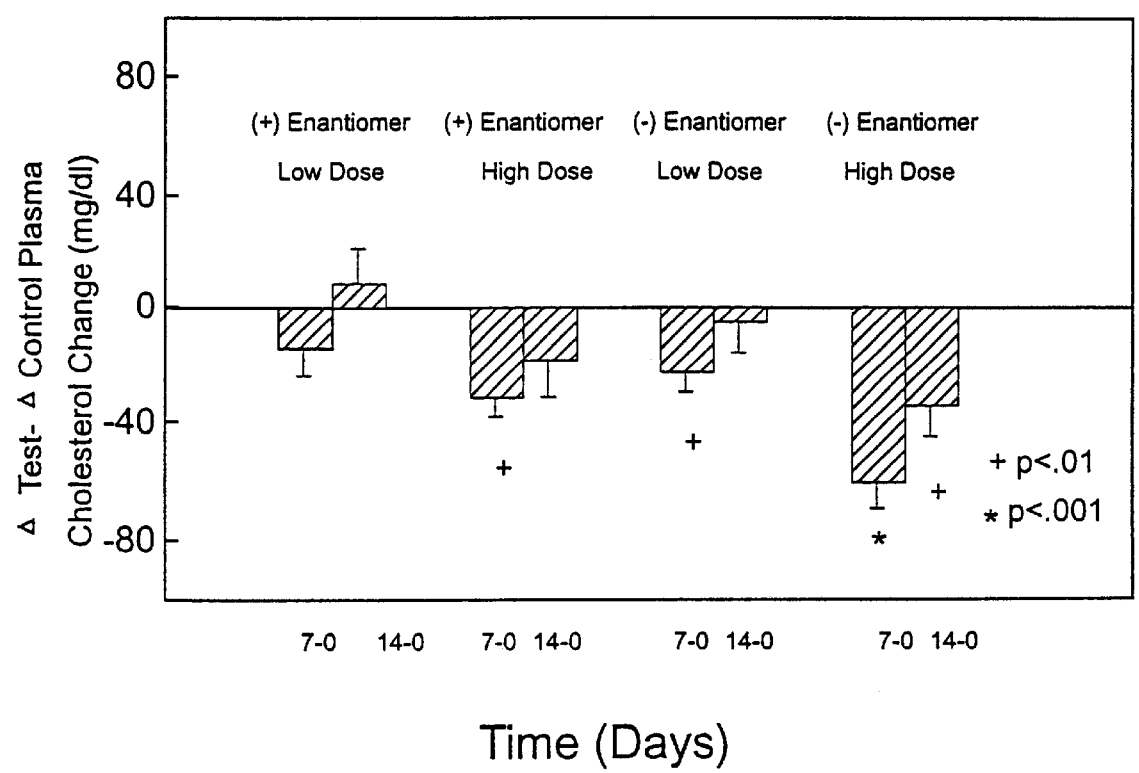
FIG. 10B compares the differences in plasma cholesterol between the control and treated groups. There were significant differences in the animals treated with the (−) enantiomer after 7 days at the low dose and after both 7 and 14 days at the high dose. The (+) enantiomer showed significance only after 7 days of treatment at the high dose.
Figure 11A:
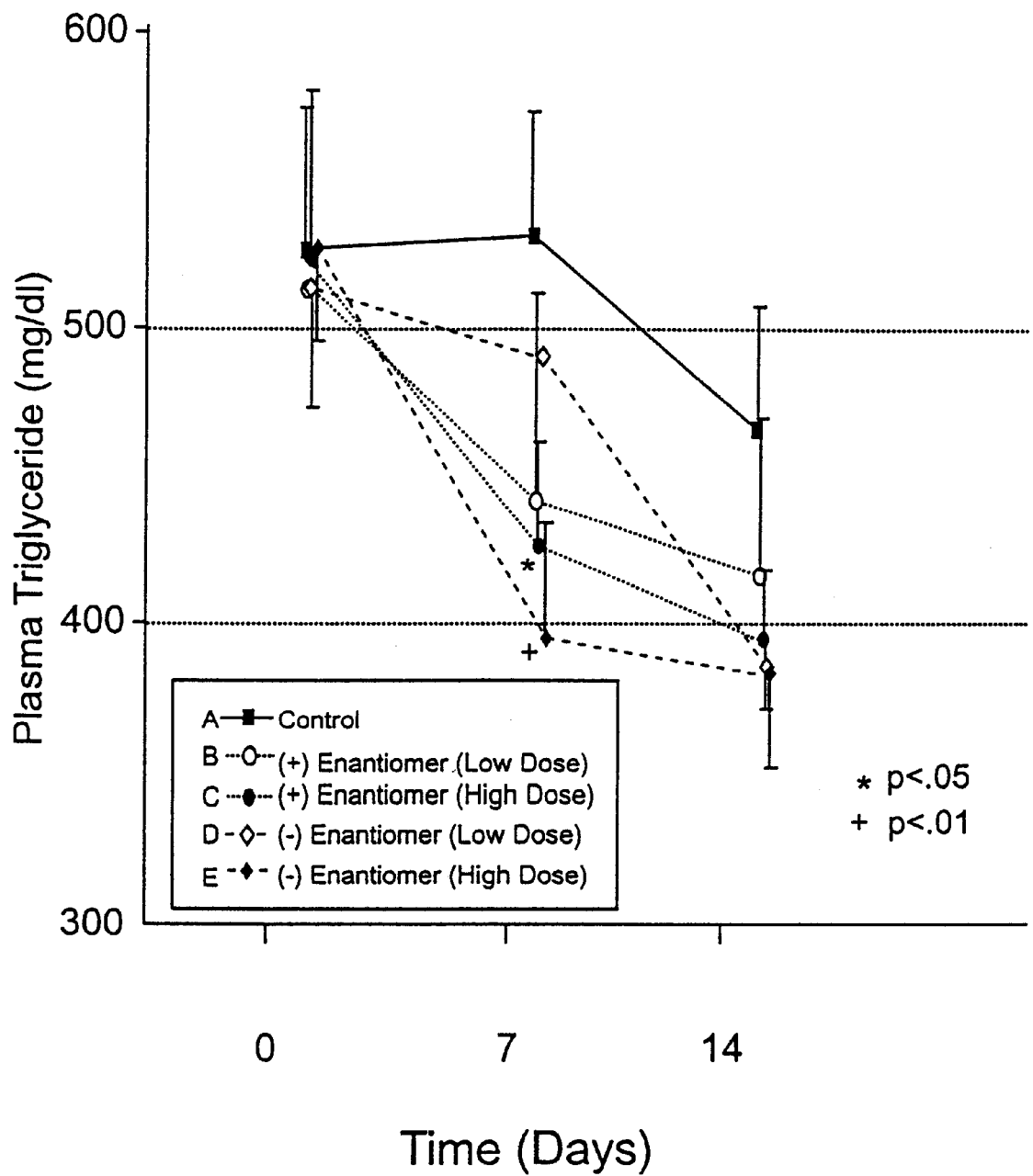
FIG. 11A shows plasma triglyceride levels in Zucker Diabetic Fatty rats treated with either (−) enantiomer or (+) enantiomer at either 12.5 mg/kg/day (Low dose) or 37.5 mg/kg/day (High dose) relative to a vehicle treated control group. Animals treated with the high dose of the (−) enantiomer had the lowest triglyceride levels of all the treatment groups.
Figure 11B:
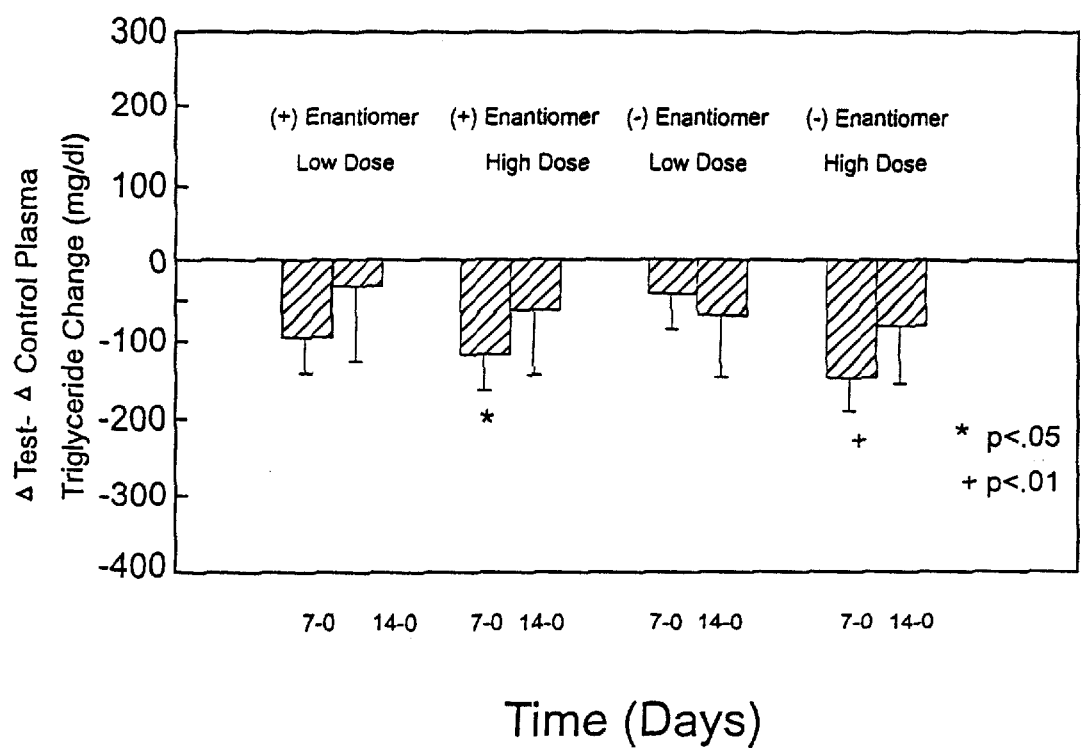
FIG. 11B compares the differences in plasma triglyceride between the control and treated groups. At 7 days, the high dose of both the (+) and (−) enantiomers showed significant lowering of plasma triglyceride.

In experiment I animals received a dose of 25 mg/kg/day. As shown in FIG. 9A and FIG. 9B, a significant decrease in plasma cholesterol was noted only in animals treated with the (−)halofenate after 7 and 13 days of treatment. In Experiment II, animals at 107 days of age received daily doses of either 12.5 mg/kg/day or 37.5 mg/kg/day of the (−) and (+) enantiomers of halofenate. As shown in FIG. 10A and FIG. 10B, the plasma cholesterol was significantly lower on the high dose after 7 days but not after 14 days of treatment with the (+) halofenate. In contrast, for the (−) halofenate at the low dose, a significant decrease in cholesterol was observed after 7 days. At the high dose a much greater decline in plasma cholesterol was noted that was apparent both after 7 and 14 days of treatment. As shown in FIG. 11A and FIG. 11B, a significant decrease in plasma triglyceride was also noted 7 days after treatment at the high dose which was of greater magnitude in animals treated with the (−) enantiomer of halofenate.

Although the foregoing invention has been described in detail for purposes of clarity of understanding, it will be obvious that certain modifications can be practiced within the scope of the appended claims. All publications and patent documents cited herein are hereby incorporated by reference in their entirety for all purposes to the same extent as if each were so individually denoted.

What is claimed is:

1. A method of treating Type 2 diabetes in a mammal, comprising: administering to said mammal a therapeutically effective amount of the (−) stereoisomer of a compound of the following formula:

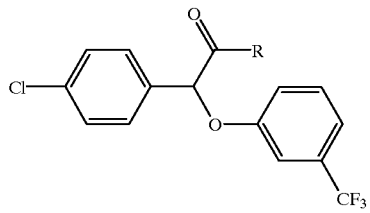

wherein:
R is a member selected from the group consisting of a hydroxy or lower alkanamido lower alkoxy; or
a pharmaceutically acceptable salt thereof,
wherein the compound is substantially free of its (+) stereoisomer.

2. The method of claim 1, wherein R is a hydroxy.

3. The method of claim 1, wherein the compound is (−) 2-acetamidoethyl 4-chlorophenyl-(3-trifluoromethylphenoxy)acetate.

4. The method of claim 1, wherein the compound is administered in combination with a compound selected from the group consisting of: a sulfonylurea or other insulin secretogogue, a thiazolidinedione, a fibrate, a HMG-CoA reductase inhibitor, a biguanide, a bile acid binding resin, nicotinic acid, a α-glucosidase inhibitor, and insulin.

5. A method of treating hyperlipidemia in a mammal, comprising administering to said mammal a therapeutically effective amount of the (−) stereoisomer of a compound of the following formula:

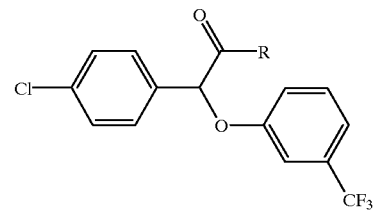

wherein:
R is a member selected from the group consisting of a hydroxy or lower alkanamido lower alkoxy; or
a pharmaceutically acceptable salt thereof, wherein the compound is substantially free of its (+) stereoisomer.

6. The method of claim 5, wherein R is a hydroxy.

7. The method of claim 5, wherein the compound is (−) 2-acetamidoethyl 4-chlorophenyl-(3-trifluoromethylphenoxy)acetate.

8. The method of claim 5, wherein the compound is administered in combination with a compound selected from the group consisting of: a sulfonylurea or other insulin secretogogue, a thiazolidinedione, a fibrate, a HMG-CoA reductase inhibitor, a biguanide, a bile acid binding resin, nicotinic acid, a α-glucosidase inhibitor, and insulin.

9. A pharmaceutical composition comprising a pharmaceutically acceptable carrier and a therapeutically effective amount of the (−) stereoisomer of a compound of the following formula:

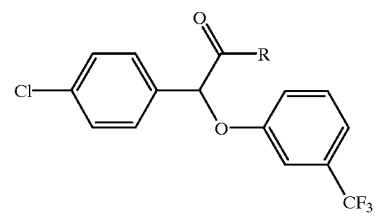

wherein:
R is a member selected from the group consisting of a hydroxy or lower alkanamido lower alkoxy; or
a pharmaceutically acceptable salt thereof, wherein the compound is substantially free of its (+) stereoisomer.

10. The pharmaceutical composition of claim 9, wherein R is a hydroxy.

11. The pharmaceutical composition of claim 9, wherein the compound is (−) 2-acetamidoethyl 4-chlorophenyl-(3-trifluoromethylphenoxy)acetate.

* * * * *

UNITED STATES PATENT AND TRADEMARK OFFICE
CERTIFICATE OF CORRECTION

PATENT NO.     : 6,262,118 B1
DATED          : July 17, 2001
INVENTOR(S)    : Kenneth L. Luskey and Jian Luo It is certified that error appears in the above-identified patent and that said Letters Patent is hereby corrected as shown below:

<u>Title page,</u>
Item [73], Assignee, replace "MetaBolex, Inc." with -- Metabolex, Inc. --

<u>Drawings,</u>
Fig 1, change "Halofenc" to -- Halofenic --

<u>Column 8,</u>
Line 57, replace "$RbA_{1a2}$" with -- $HbA_{1a2}$ --.

<u>Column 10,</u>
Line 34, delete "of the" (second occurrence)

<u>Column 14,</u>
Line 56, after "thereof" insert -- . --

Signed and Sealed this

Twenty-seventh Day of August, 2002

Attest:

Attesting Officer

JAMES E. ROGAN
Director of the United States Patent and Trademark Office